(12) United States Patent
Hansen et al.

(10) Patent No.: US 8,362,402 B2
(45) Date of Patent: Jan. 29, 2013

(54) FLUID WARMER WITH SWITCH ASSEMBLY

(75) Inventors: William J. Hansen, Pewaukee, WI (US); Terence T. Smith, Waukesha, WI (US)

(73) Assignee: Enthermics Medical Systems, Inc, Menomonee Falls, WI (US)

( * ) Notice: Subject to any disclaimer, the term of this patent is extended or adjusted under 35 U.S.C. 154(b) by 277 days.

(21) Appl. No.: 12/838,872

(22) Filed: Jul. 19, 2010

(65) Prior Publication Data
US 2010/0276411 A1 Nov. 4, 2010

Related U.S. Application Data

(63) Continuation-in-part of application No. 12/208,166, filed on Sep. 10, 2008, now Pat. No. 8,076,618.

(51) Int. Cl.
*F27D 11/00* (2006.01)
*H05B 3/68* (2006.01)
(52) U.S. Cl. .............. 219/385; 219/443.1; 219/446.1
(58) Field of Classification Search .......... None
See application file for complete search history.

(56) References Cited

U.S. PATENT DOCUMENTS

| | | | |
|---|---|---|---|
| 5,408,576 A | 4/1995 | Bishop | |
| 5,733,263 A | 3/1998 | Wheatman | |
| 5,875,282 A * | 2/1999 | Jordan et al. | 392/470 |
| 6,142,974 A | 11/2000 | Kistner et al. | |
| 6,259,067 B1 | 7/2001 | Faries, Jr. et al. | |
| 6,294,762 B1 | 9/2001 | Faries, Jr. et al. | |
| 6,376,805 B2 | 4/2002 | Faries, Jr. et al. | |
| 6,384,380 B1 | 5/2002 | Faries, Jr. et al. | |
| 6,467,953 B1 | 10/2002 | Faries, Jr. et al. | |
| 6,566,631 B2 | 5/2003 | Faries, Jr. et al. | |
| 6,660,974 B2 | 12/2003 | Faries, Jr. et al. | |
| 6,722,782 B2 | 4/2004 | Faries, Jr. et al. | |
| 6,768,085 B2 | 7/2004 | Faries, Jr. et al. | |
| 6,824,528 B1 | 11/2004 | Faries, Jr. et al. | |
| 6,861,624 B1 | 3/2005 | Pelster | |
| 6,869,538 B2 | 3/2005 | Yu et al. | |
| 7,010,221 B2 | 3/2006 | Augustine et al. | |
| RE39,075 E | 4/2006 | Verkaart | |
| 7,031,602 B2 | 4/2006 | Faries, Jr. et al. | |
| 7,041,941 B2 | 5/2006 | Faries, Jr. et al. | |

(Continued)

FOREIGN PATENT DOCUMENTS

DE 19752578 A1 6/1999

OTHER PUBLICATIONS

Extended European Search Report for corresponding application EP10172181, dated Aug. 19, 2011 [7 pages].

(Continued)

*Primary Examiner* — Scott B Geyer
(74) *Attorney, Agent, or Firm* — Boyle Fredrickson S.C.

(57) ABSTRACT

A fluid warmer is disclosed. The fluid warmer includes a support surface, a heating element configured to selectively heat the support surface, and a switch assembly extending through the support surface. The switch assembly includes a switch, a movable switch plate, and a thermocouple. The switch has at least two states, one of which indicates the presence of an item on the support surface. The movable switch plate operably links to the switch to move the switch between the states and further includes a contact surface that contacts an item placed on the support surface. One or more thermocouples are embedded in the movable switch plate below the contact surface. The movable switch plate comprises a material having a thermal conductivity that permits the thermocouple(s) embedded in the switch plate to measure a temperature of an item placed on the support surface within a predetermined period of time.

19 Claims, 17 Drawing Sheets

U.S. PATENT DOCUMENTS

| | | |
|---|---|---|
| 7,090,658 B2 | 8/2006 | Faries, Jr. et al. |
| 7,128,275 B2 | 10/2006 | Kammer et al. |
| 7,153,285 B2 | 12/2006 | Lauman et al. |
| 7,158,719 B2 | 1/2007 | Cassidy |
| D546,943 S | 7/2007 | Kammer et al. |
| D546,944 S | 7/2007 | Kammer et al. |
| D547,444 S | 7/2007 | Kammer et al. |
| 7,238,170 B2 | 7/2007 | Park |
| 7,238,171 B2 | 7/2007 | Faries, Jr. et al. |
| 7,276,675 B2 | 10/2007 | Faries, Jr. et al. |
| 7,307,245 B2 | 12/2007 | Faries, Jr. et al. |
| 7,326,882 B2 | 2/2008 | Faries, Jr. et al. |
| D568,989 S | 5/2008 | Kammer et al. |
| D569,970 S | 5/2008 | Kammer et al. |
| 7,441,714 B2 | 10/2008 | Kammer et al. |
| 7,459,657 B2 | 12/2008 | Kammer et al. |
| 7,540,864 B2 | 6/2009 | Faries, Jr. et al. |
| 7,560,667 B2 | 7/2009 | Kammer et al. |
| 7,854,387 B2 * | 12/2010 | Kammer et al. ............ 236/1 C |
| 2001/0042743 A1 | 11/2001 | Faries, Jr. et al. |
| 2002/0021741 A1 | 2/2002 | Faries, Jr. et al. |
| 2002/0158058 A1 | 10/2002 | Faries, Jr. et al. |
| 2003/0000939 A1 | 1/2003 | Faries, Jr. et al. |
| 2004/0188409 A1 | 9/2004 | Faries, Jr. et al. |
| 2004/0247016 A1 | 12/2004 | Faries, Jr. et al. |
| 2006/0086361 A1 | 4/2006 | Kammer et al. |
| 2006/0289016 A1 | 12/2006 | Kammer et al. |
| 2006/0291533 A1 | 12/2006 | Faries, Jr. et al. |
| 2007/0000910 A1 | 1/2007 | Faries, Jr. et al. |
| 2007/0015975 A1 | 1/2007 | Faries, Jr. et al. |
| 2008/0152937 A1 | 6/2008 | Kammer et al. |
| 2008/0272199 A1 | 11/2008 | Kammer et al. |

OTHER PUBLICATIONS

Midmark, iWarm IV Fluid Warmer, http://www.midmark.com/Pages/Product.aspx?iProductID=398&iHierarchyID=4214&cat=monitoringandcriticalcare, printed as of Jun. 30, 2010 (1 page).

Paragon Medical: Fluid Warmers, http://www.paragonmed.com/fluidwarm.shtml, printed as of Jul. 16, 2010 (3 pages).

Hotline Blood and Fluid Warmer, http://www.smiths-medical.com/catalog/fluid-warming/low-flow-hotline/hardware/hotline-blood-fluid-warmer.html, printed as of Jun. 30, 2010 (9 pages).

Thermal Angel Blood and IV Fluid Infusion Warmer, http://www.thermalangel.com/html/products/thermal-angel/index/, printed as of Jun. 30, 2010 (3 pages).

A Hypothermia Treatment Technology Web Site, Model 3000 Intravenous Fluid Warmer, http://www.hypothermia-ca.com/IV-warmer.html, printed as of Jun. 30, 2010 (6 pages).

Smithworks Medical, Inc., Floor Mount, We've Got You Covered, http://www.smithworksmedical.com/us/?page_id=8, printed as of Jun. 30, 2010 (3 pages).

Vital-Signs, enFlow IV Fluid/Blood Warming System, http://www2.vital-signs.com/vsihome/html/english/products/critical/enFlowFluidWarming.aspx, printed as of Jun. 30, 2010 (3 pages).

PCT International Search Report for PCT/US2009/056464, mailed Feb. 4, 2010 (2 pages).

* cited by examiner

FLUID WARMER WITH SWITCH ASSEMBLY

CROSS-REFERENCE TO RELATED APPLICATION

This patent application is a continuation-in-part of U.S. patent application Ser. No. 12/208,166 filed on Sep. 10, 2008, now U.S. Pat. No. 8,076,618 the disclosures of which is hereby incorporated by reference as if set forth in its entirety herein.

STATEMENT OF FEDERALLY SPONSORED RESEARCH OR DEVELOPMENT

Not applicable.

BACKGROUND OF THE INVENTION

This invention relates to the heating of a fluid disposed in a container. In particular, this invention relates devices and methods for the efficient heating of a fluid prior to its introduction into a body.

During medical care, it may be necessary to introduce a fluid into a human body intravenously. Such fluids may include, for example, blood, saline solution, antibiotic solution, and the like. Prior to administration, these fluids are usually stored in containers such as bags or bottles.

However, many of these fluid degrade at room temperature when outside of a body. Since the demand for many of these fluids is unpredictable (e.g., due to the nature of emergency conditions), it is preferable to maintain an inventory of many of these fluids within a hospital.

To prevent the degradation and to maintain the efficacy of such fluids, the fluids are conventionally refrigerated or frozen. Then, as needed, the fluids are warmed prior to their administration. In cases where large amounts of fluid are introduced to the body intravenously over a short period of time, it may be necessary to warm these fluids close to body temperature (around 98.6° F.) to prevent the patient from entering a hypothermic condition.

Conventionally, a hospital has an oven with a large capacity that heats the fluid containers prior to use. Usually, this oven is designed to have sufficient excess capacity to warm enough containers to satisfy the needs of the hospital in a worse case scenario. However, more frequently, only a fraction of the capacity of the oven is utilized. This under-utilization of the volume of the oven means that it may take longer to heat the entire volume up to the desired temperature and that energy is lost when the oven is at less than capacity.

Further, when a container is placed in the oven, it must be tagged or in some way monitored to ensure that the fluid does not stay in the oven too long and spoil. Particularly, when an oven warms multiple containers at once, there must be a system in place that determines the length of time that a particular container has been in the oven.

Hence, a need exists for an improved fluid warmer that more efficiently heats fluids prior to use in the body as well as tracks their thermal history.

SUMMARY OF THE INVENTION

An improved fluid warmer is disclosed. The fluid warmer includes a support surface, a heating element configured to selectively heat the support surface, and a switch assembly extending through the support surface. The switch assembly includes a switch, a movable switch plate, and one or more thermocouples. The switch has at least two states, one of which indicates the presence of an item on the support surface. The movable switch plate operably links to the switch to move the switch between states and includes a contact surface that contacts an item placed on the support surface. One or more thermocouples are embedded in the movable switch plate below the contact surface. The movable switch plate comprises a material having a thermal conductivity that permits the thermocouple(s) embedded in the switch plate to measure a temperature of an item placed on the support surface within a predetermined period of time.

In some forms of the fluid warmer, the movable switch plate may include a heat conducting member having an end of the thermocouple is embedded therein. This heat conducting member may also form at least a portion of the contact surface of the movable switch plate. The heat conducting member may comprise a material having a thermal conductivity exceeding 200 $W \cdot m^{-1} \cdot K^{-1}$, which in some forms may be copper or a copper alloy.

In other forms of the fluid warmer, the movable switch plate may include a first portion and a second portion. A cavity may be formed in the second portion that receives the first portion. The first portion may have at least one bay formed therein that receives an end of the thermocouple. When the first portion is received in the second portion, a space may be defined between the first portion and the second portion. The second portion may further include a passage running from the cavity through the second portion, thereby providing a pathway for a wire of the thermocouple from the at least one bay in the first portion, through the space between the first portion and the second portion, and through the passage in the second portion to an exterior of the movable switch plate.

In some forms, the switch may be a microswitch and/or the movable switch plate may include a downwardly extending projection that engages an actuatable part of the switch or microswitch.

In other forms, an air gap may separate the movable switch plate from the support surface of the fluid warmer, thereby thermally isolating the movable switch plate from the support surface of the fluid warmer.

In yet other forms of the fluid warmer, the switch assembly may further include a switch housing that supports the switch and the movable switch plate. The movable switch plate may be pivotally attached to the switch housing by a pivot pin. A flange in the switch housing may be configured to position the switch assembly relative to a support surface of the fluid warmer such that the contact surface of the movable switch plate resides above the support surface.

The switch and movable switch plate may constitute a presence sensor configured to detect a presence of the item on the contact surface. The presence sensor may provide a signal indicating the item is disposed on the contact surface and the thermocouple may provide a signal indicating a temperature of the item disposed on the contact surface.

A switch assembly is also disclosed for use in a support surface of a fluid warmer. This switch assembly includes a presence sensor configured to detect a presence of an item engaging a contact surface of the presence sensor and a thermocouple embedded in the presence sensor below the contact surface. The presence sensor provides a signal indicating the item is disposed on the support surface of the fluid warmer and the thermocouple provides a signal indicating a temperature of the item disposed on the contact surface. The contact surface of presence sensor comprises a material having a thermal conductivity that permits the thermocouple embedded in the presence sensor to measure the temperature of the item on the contact surface within a predetermined period of time. Further, the material of the contact surface is thermally isolated from the support surface of the fluid warmer.

In some forms of the switch assembly, the presence sensor may include a switch having at least two states and a movable switch plate operably linked to the switch to move the switch between the at least two states depending on a presence of an item on the contact surface of the movable switch plate.

The presence sensor may comprise a heat conducting member in which an end of the thermocouple is embedded. The heat conducting member may also form at least a portion of the contact surface of the presence sensor. The heat conducting member may comprise a material having a thermal conductivity exceeding 200 W·m$^{-1}$·K$^{-1}$.

Thus, a fluid warmer and a switch assembly are disclosed that are able to both detect the presence and the temperature of an item, such as a bag of fluid, on a contact surface of the switch assembly. The portion of the switch assembly which directly contacts the item may be made of a highly thermally conductive material, such as copper, so that one or more thermocouples embedded below the contact surface may quickly and accurately measure the temperature of the item on the switch assembly.

Notably, the switch assembly integrates the thermocouple into the same part of the structure that detects the presence of the item. As a result, the overall footprint of the presence and temperature sensors on the support surface is minimized. Further, as the thermocouple in the switch assembly is thermally isolated from the support surface of the fluid warmer (i.e., the thermocouple is not directly supported by the support surface, but is rather located in the heat conducting member of the switch assembly which is isolated from the heated support surface), the thermocouple obtains a more accurate reading of the item on the fluid warmer and not the temperature of the heated support surface.

These and still other advantages of the invention will be apparent from the detailed description and drawings. What follows is merely a description of some preferred embodiments of the present invention. To assess the full scope of the invention the claims should be looked to as the preferred embodiments are not intended to be the only embodiments within the scope of the claims.

DETAILED DESCRIPTION OF THE PREFERRED EMBODIMENTS

Figure 1:
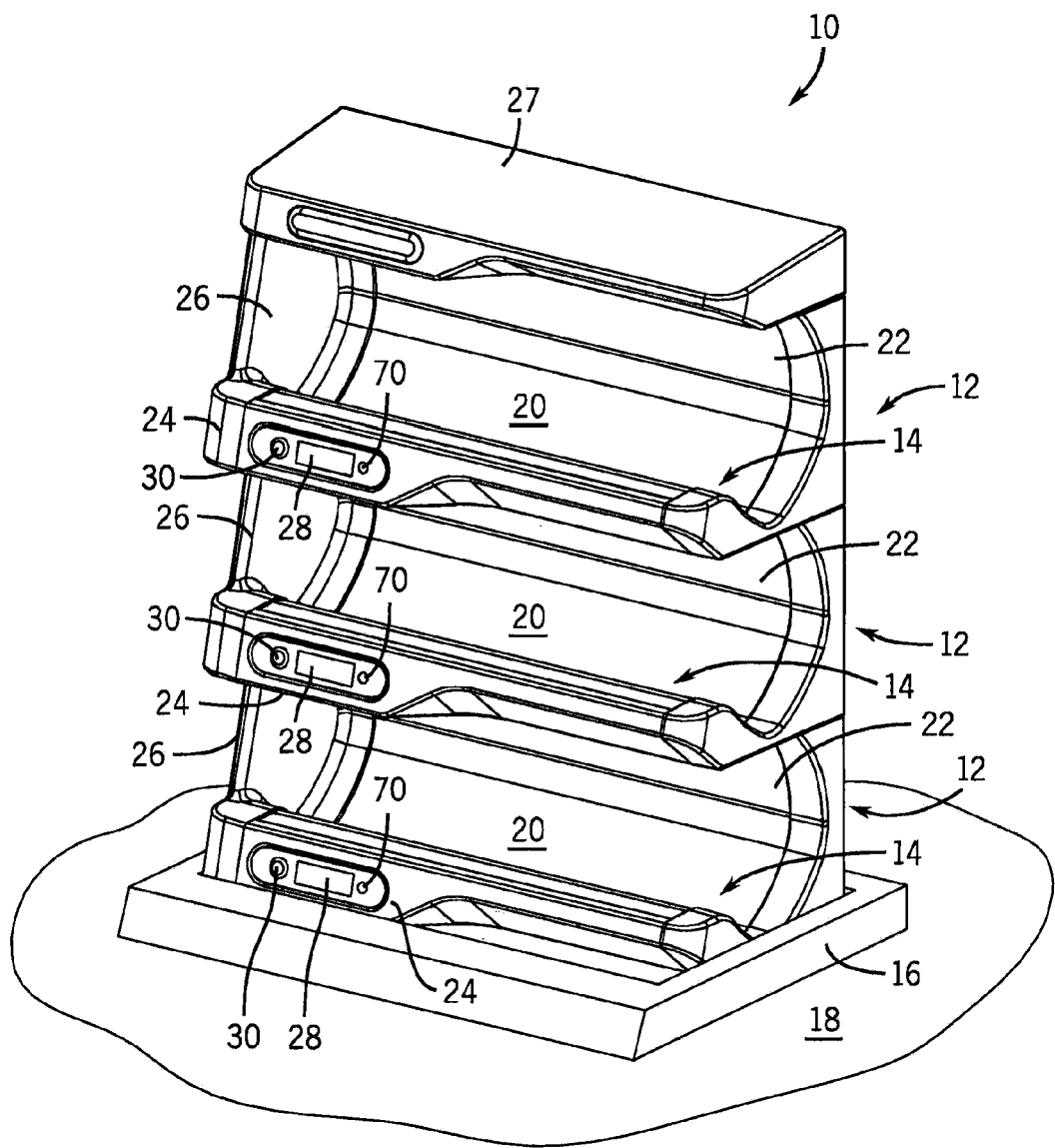
FIG. 1 is an environmental view of a stacked assembly of modular fluid warmers docked in a countertop pedestal.

Referring first to FIG. 1, a stacked assembly 10 is composed of a number of modular fluid warmers 12. As shown, the modular fluid warmers 12 are stacked three high, thus providing three shelves 14 for the placement of the containers. Although the stacked assembly 10 is shown as containing three modular fluid warmers 12, it should be appreciated that the stacked assembly 10 can include one or more modular fluid warmers 12. As shown in FIG. 1, the stacked assembly 10 is docked in a countertop pedestal 16 that rests on the surface of a table 18.

Each of the modular fluid warmers 12 form shelves 14 having support surfaces 20 for the placement of a container (not shown), such as a bag or bottle, that is filled with fluid. As can be seen best in FIG. 3, the support surface 20 is essentially C-shaped for receiving the bag or bottle. Although essentially C-shaped, the support surface 20 also has a portion that is flat with a bend so as to better receive bottles having a generally square-shaped cross-section or a relatively rigid flat surface. The support surface 20 is part of a support structure 22 which will be described in further detail below with respect to FIGS. 7 and 8. The support surface 20 is heated by a heating element 23 (best seen in FIGS. 3, 7, and 8), which is attached to the underside of the support surface 20.

The support structure 22 of each of the modular fluid warmers 12 is substantially surrounded by a casing 24. The casing 24 may be formed of a engineered plastic material that does not deform at room temperature to slightly above room temperature (50° F. to approximately 175° F.). On the left side of each of the modular fluid warmers 12, there is a side wall 26 that is integrally formed with the casing 24. On the top of the stacked assembly 10, a top casing 27 hangs over the top shelf.

At least one benefit of the modular fluid warmers 12 as shown, is that the shelves 14 provide easy access to the support surface 20 for the placement or the removal of a container. Thus, it is not necessary to open or close a door to load or remove a container from the support surface 20. Although a door could be present to form a compartment or chamber that retains heat, such a door is not deemed necessary in the present invention given the location of the heating elements and method of warming.

Each of the modular fluid warmers 12 have a display 28 with a recall button 30. This display 28 can be used display whether or not a container is sensed on the support surface 20, temperature information (e.g., the temperature of the container being heated), or time information (e.g., the time that the container being heated has been at the desired temperature). In one form, when the shelf 14 is empty, the display 28 will display four horizontal dashed lines. This indicates to a user that the modular fluid warmer 12 is operating and ready to receive a container. When the shelf 14 is occupied, the display 28 will show a scrolling vertical line to indicate that the bag or bottle has been sensed on the shelf 14. The recall button 30 may be depressed to indicate the time or the time at temperature. To achieve this functionality, there may be more than one recall button or depressing the recall button 30 may cause the display 28 to cycle through the available data (i.e., the first press of the recall button provides the temperature of the item, the second press provides the time at temperature, the third press indicates the detection status of an item, and so forth). Although one form of operational information recall has been disclosed, other ways of displaying and recalling information could also be employed.

Referring now to FIGS. 2A-2D and FIG. 3, a series of steps for assembling the stacked assembly 10 is shown. In general, the stacked assembly 10 is formed by attaching individual modular fluid warmers 12 to a back plate 32 that is sized to receive the desired number of modular fluid warmers 12. In this particular assembly, the stacked assembly 10 is only two modular fluid warmers high. However, as stated above, the back plate 32 could be sized to receive any number of modular fluid warmers 12.

The back plate 32 will now be described in detail. The back plate 32 includes a back wall 34 having two side walls 36 and a top wall 38 extending forward therefrom. The two side walls 36 and the top wall 38 also meet along edges to form a top of the stacked assembly 10. On one of the side walls 36, near the top of the back plate 32, there is a power switch 40 which will be used to toggle power to all of the modular fluid warmers 12 that are attached to the back plate 32. The back wall 34 includes sets of tabs 42 that extend forward and upward for receiving the modular fluid warmers 12. The back wall 34 contains a number of other apertures including screw holes 44 for securing screws through the back plate 32 and into the modular fluid warmers 12 and mounting holes 46 for securing the stacked assembly 10 to a wall or the like.

Figure 3:
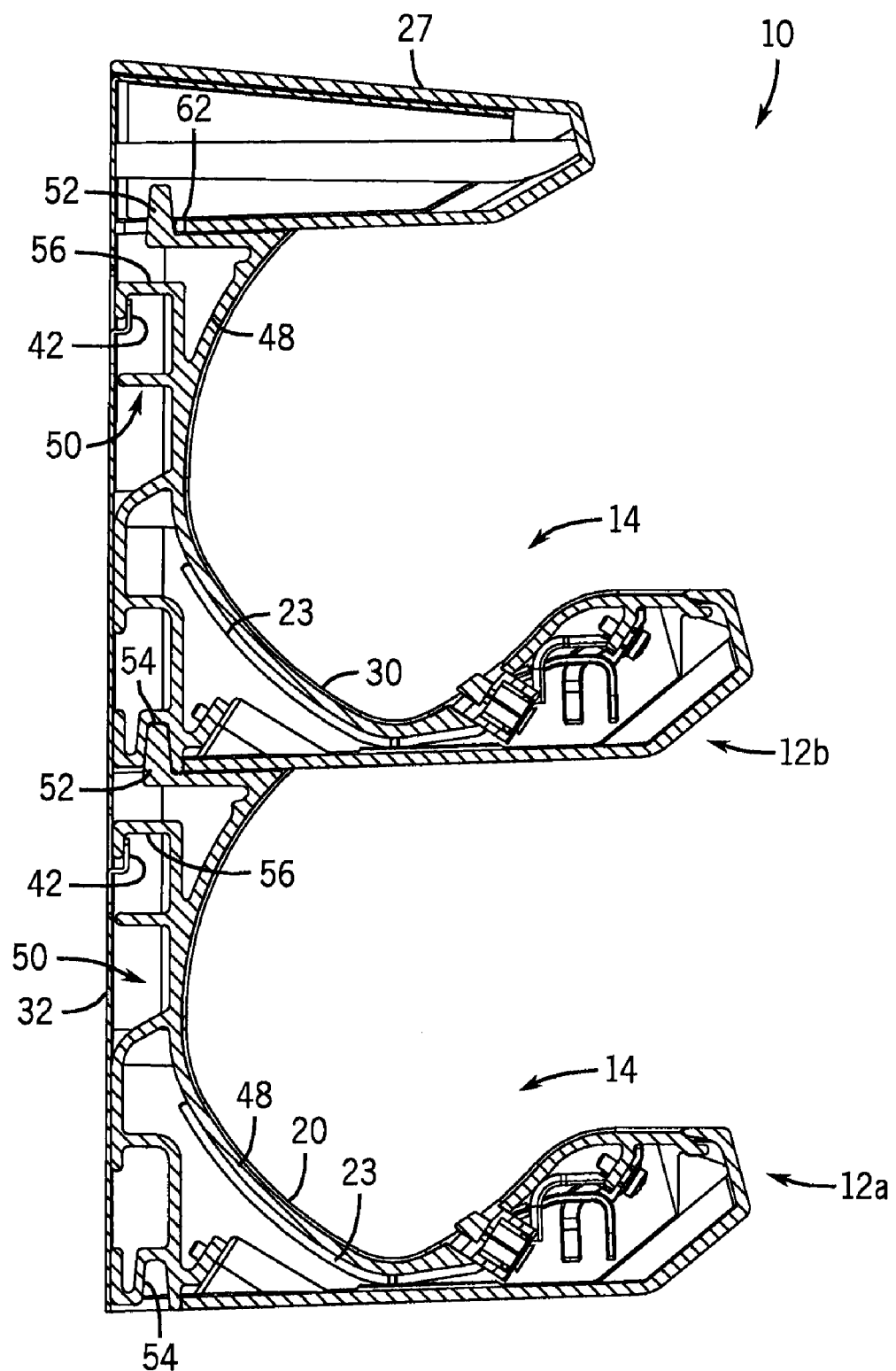
FIG. 3 is a cross sectional view of the stacked assembly of FIG. 2D.

As best seen in FIG. 3, each of the modular fluid warmers 12 include a support structure 22. The support structure 22 includes an essentially C-shaped portion 48 which serves as the support surface 20 and shelf for receiving the container to be heated. The support structure 22 further includes a back wall portion 50 that supports the shelf and includes many features required to form the stacked assembly 10. In the form shown in FIGS. 7 and 8, the portions 48 and 50 are integrally formed.

On the upper surface of the back wall portion 50, a first mating structure 52 is provided in the form of a tongue. On the lower surface of the back wall portion 50, a second mating structure 54 is provided in the form of a groove that is shaped to receive the tongue. Between the top and bottom surfaces of the back wall portion 50, a tab 56 extends out and down from the back wall portion 50. This tab 56 is formed to be slid over the set of tabs 42 formed in the back plate 32. Also a number of screw holes 58 are formed on the back side of the back wall portion 50 for use during attachment of the modular fluid warmer 12 to the back plate 32.

Given the complex profile of the support structure 22, it may be formed by an extrusion process and is composed of, at least in one form, aluminum or an aluminum alloy. Although the support structure 22 is shown as being a integrally-formed component, the support structure 22 could also be formed by the attachment of two or more separate components that provide features similar to the integrally formed component.

Figure 2A:
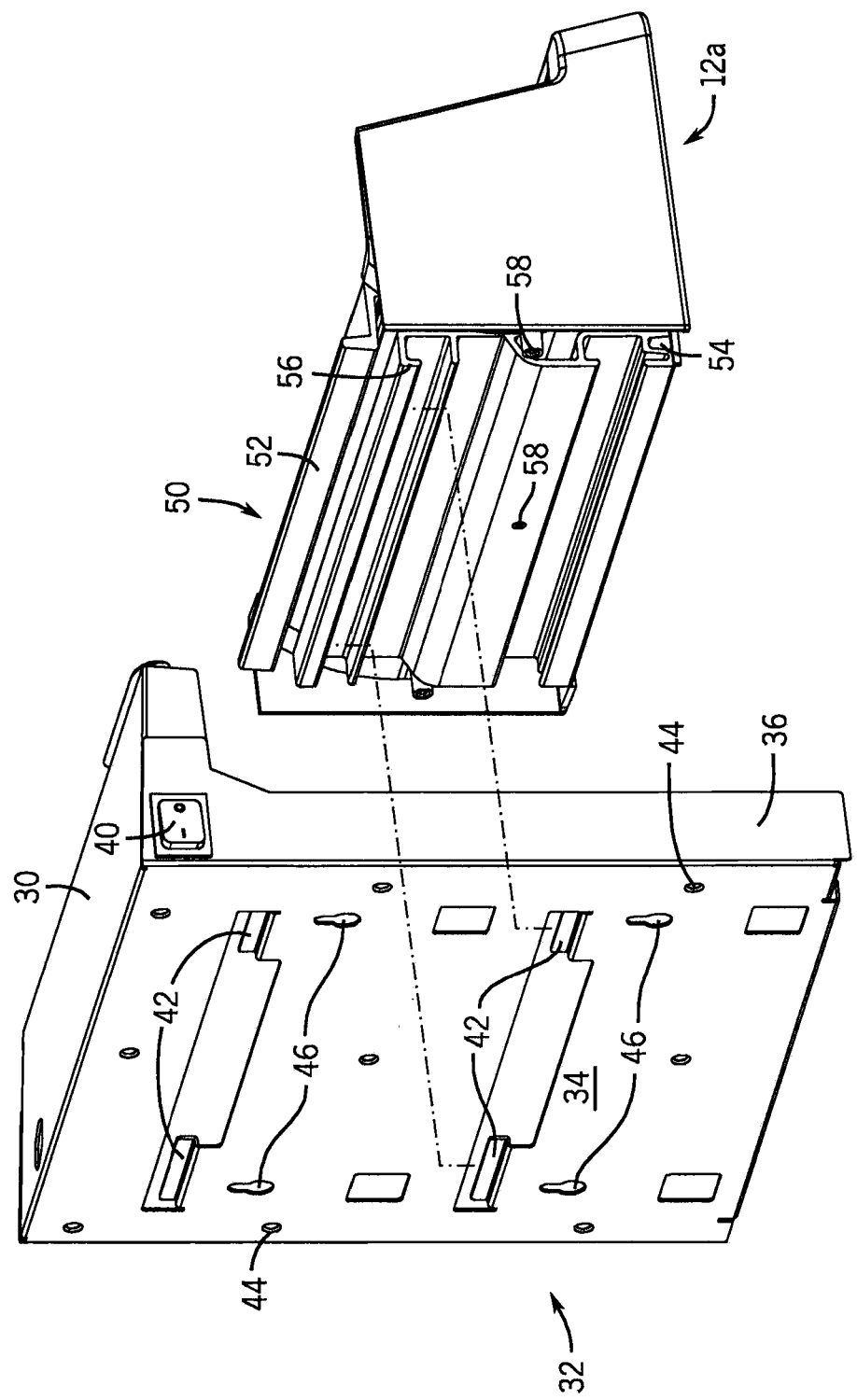
FIGS. 2A-2D are perspective views of the steps used to assemble a stacked assembly having two modular fluid warmers.

Looking first at FIG. 2A, a first modular fluid warmer 12a is attached to the lowest available reception spot on the back plate 32 by attaching the back wall portion 50 of the modular fluid warmer 12a to the back plate 32. The tab 56 of the back wall 34 of the support structure 22 is slid over and down on the set of tabs 42 on the back plate 32. When the tabs 42 and 56 engage one another, then a set of screw holes 58 on the backside of the support structure 22 align with the set of screw holes 44 on the back plate 32. Screws are then threaded through the screw holes 44 and 58 to attach the first modular fluid warmer 12a to the back plate 32. Although not shown, it is contemplated that the second mating structure 54 could engage a mating structure formed proximate the bottom of the back plate 32 to further secure the first modular fluid warmer 12a to the back plate 32.

Figure 2B:
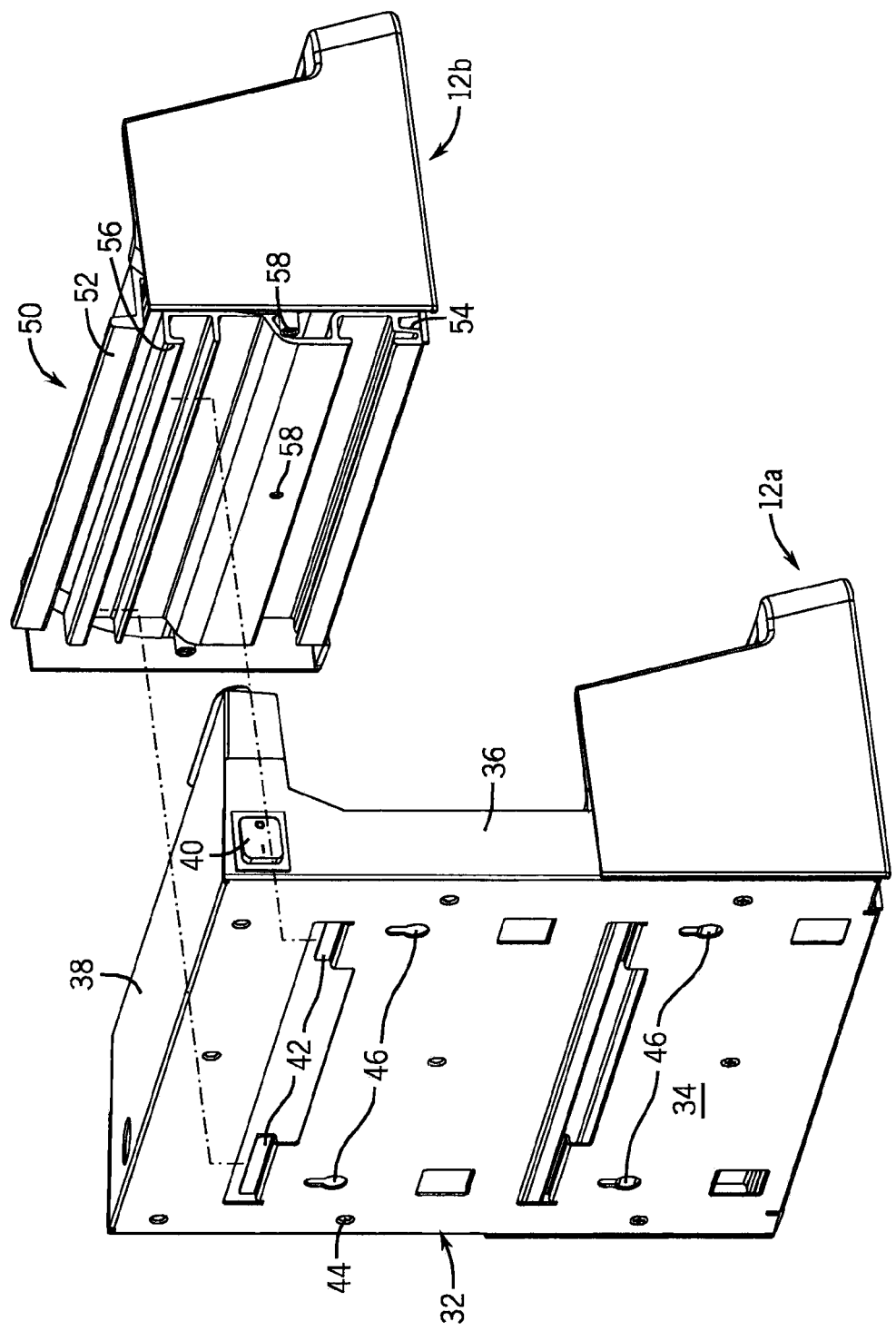

Looking now at FIG. 2B, a second modular fluid warmer 12b is shown being attached to the back plate 32 above the first modular fluid warmer 12a. The second modular fluid warmer 12b is attached to the back plate 32 in a similar fashion as the first modular fluid warmer 12a. Again, the tab 56 of the back wall portion 50 of the second modular fluid warmer 12b is attached to a set of tabs 42 on the back plate 32. Notably, as the second modular fluid warmer 12b is slid back and over the set of tabs 42, there is no interference issue between the portion of the side wall 36 of the back plate 32 and the casing 24 of the second modular fluid warmer 12b because the second modular fluid warmer 12b has a U-shaped section proximate the ends that provides clearance for the insertion. Once the second modular fluid warmer 12b is positioned on the back plate 32, the second modular fluid warmer 12b may also be secured to the back plate 32 using screws.

As best shown in FIG. 3, as the second modular fluid warmer 12b is slid down into place, the second mating structure 54 on the bottom surface of the second modular fluid warmer 12b interfits with the first mating structure 52 on the top surface of the first modular fluid warmer 12a. In the particular form shown, the groove of the second modular fluid warmer 12b is slid over the tongue of the first modular fluid warmer 12a. Although a tongue and groove connection is shown, the mating have could take on a number of different forms. In some forms, these connections may snap or lock the two modular fluid warmers together.

It is contemplated that each of the fluid warmers will receive electrical power from a power source operated by the power switch 40. Groups of wires running from the power source to each of the modular fluid warmers 12a and 12b supply power to each of the modular fluid warmers 12a and 12b. The wires may be connected to each of the modular fluid warmers 12 and 12b using either a screw terminal or a plug-type connection. It is contemplated that the modular fluid connectors could be electrically connected in either parallel or series. For ease of assembly and for improved troubleshooting if an individual modular fluid warmer fails, parallel connections may be preferable.

Further, as the modular fluid warmers 12a and 12b are stacked onto one another, they could have electrical connections that allows each of the modular fluid warmers 12a and 12b to receive power from the same power source in series or parallel.

Figure 2C:
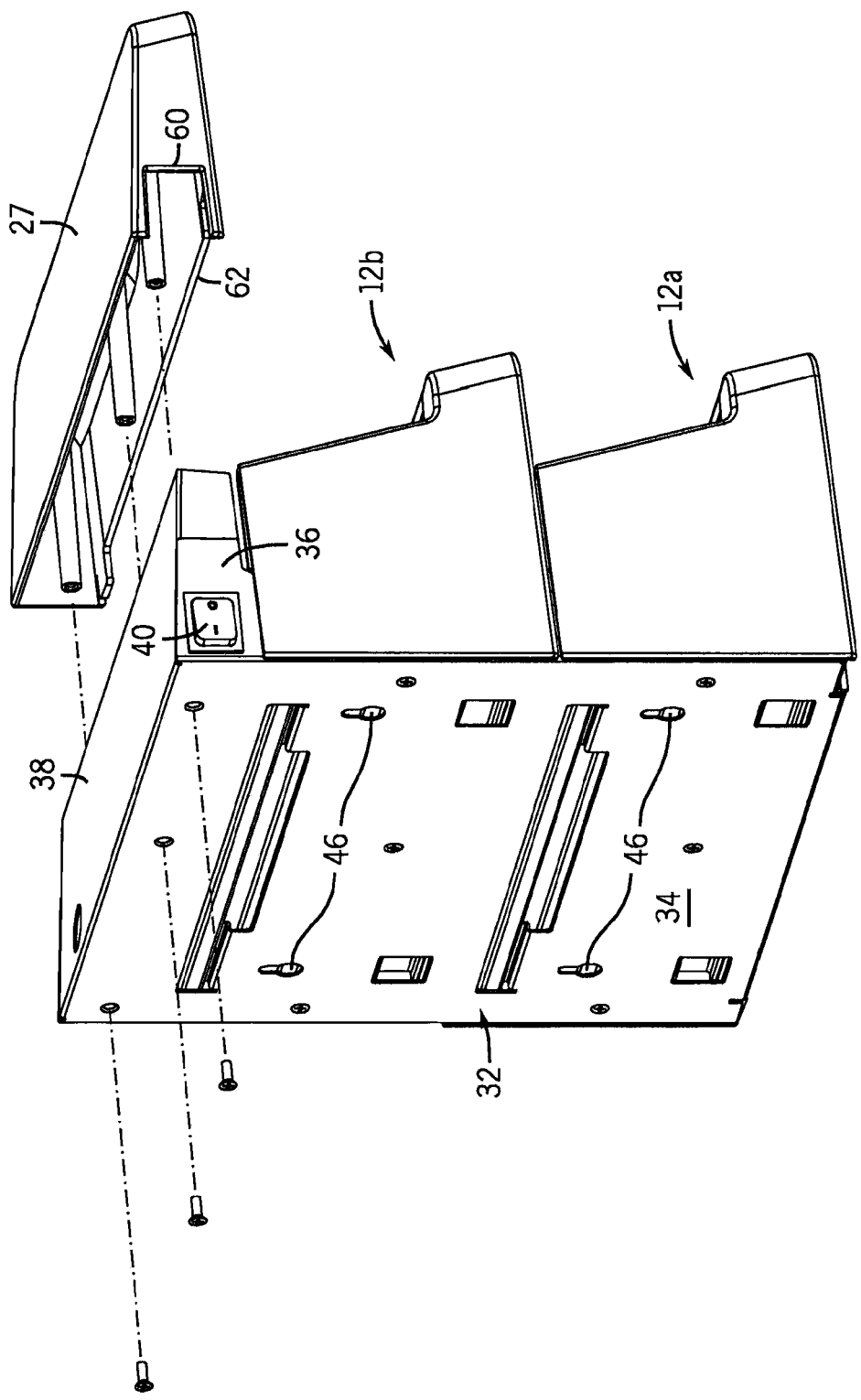
Figure 2D:
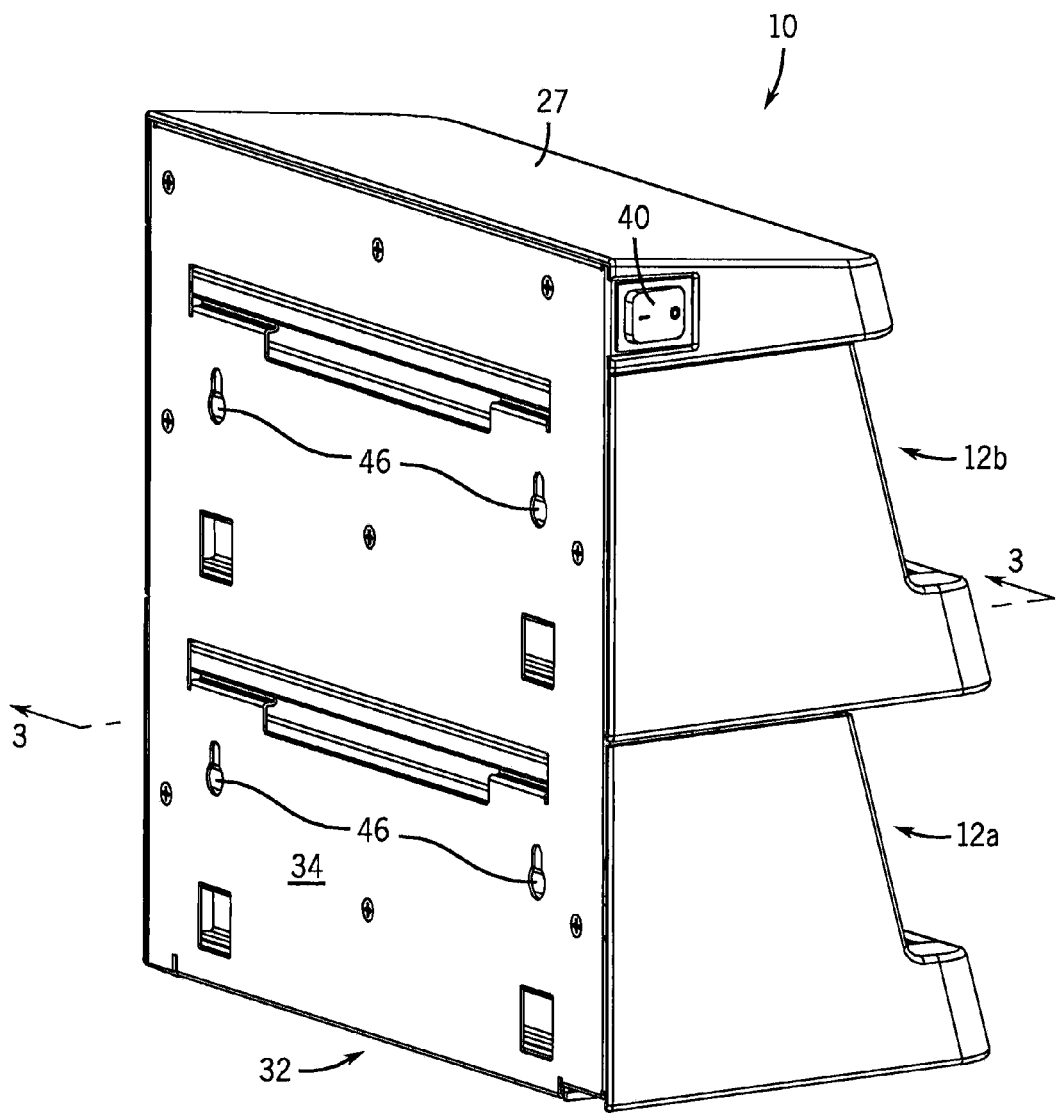

As shown in FIGS. 2C and 2D, once both of the modular fluid warmers 12a and 12b are attached to the back plate 32, the top casing 27 may be slid over the overhanging section of the back plate 32. This top casing 27 may match the outer appearance of the casing 24 of the modular fluid warmers 12a and 12b and could be used to brand the stacked assembly 10. The top casing 27 has a cutout 60 for wrapping around the power switch 40 and a bottom edge 62 that is formed to terminate prior to contacting the first mating structure 52 of the second modular fluid warmer 12b. It is contemplated that in some forms of the invention, the modular fluid warmers 12*a* and 12*b* themselves might be freely hung on the back plate 32 without screws and it is only the top casing 27, once secured to the back plate 32 with screws, that permanently retains the modular fluid warmers 12*a* and 12*b* on the back plate 32.

Although the modular fluid warmers 12*a* and 12*b* have been shown as being attached one at a time to the back plate 32, it is contemplated that the modular fluid warmers 12*a* and 12*b* could be pre-stacked and then attached to the back plate 32 as a group.

Further, although the back plate 32 has been shown as a single plate sized to accommodate a specific number of modular fluid warmers, it is contemplated that the back plate 32 may be composed of a number of plates attachable to one another. In this way, if it was desirable to increase the capacity of the stacked assembly 10, another modular fluid warmer could be easily added.

Figure 4:
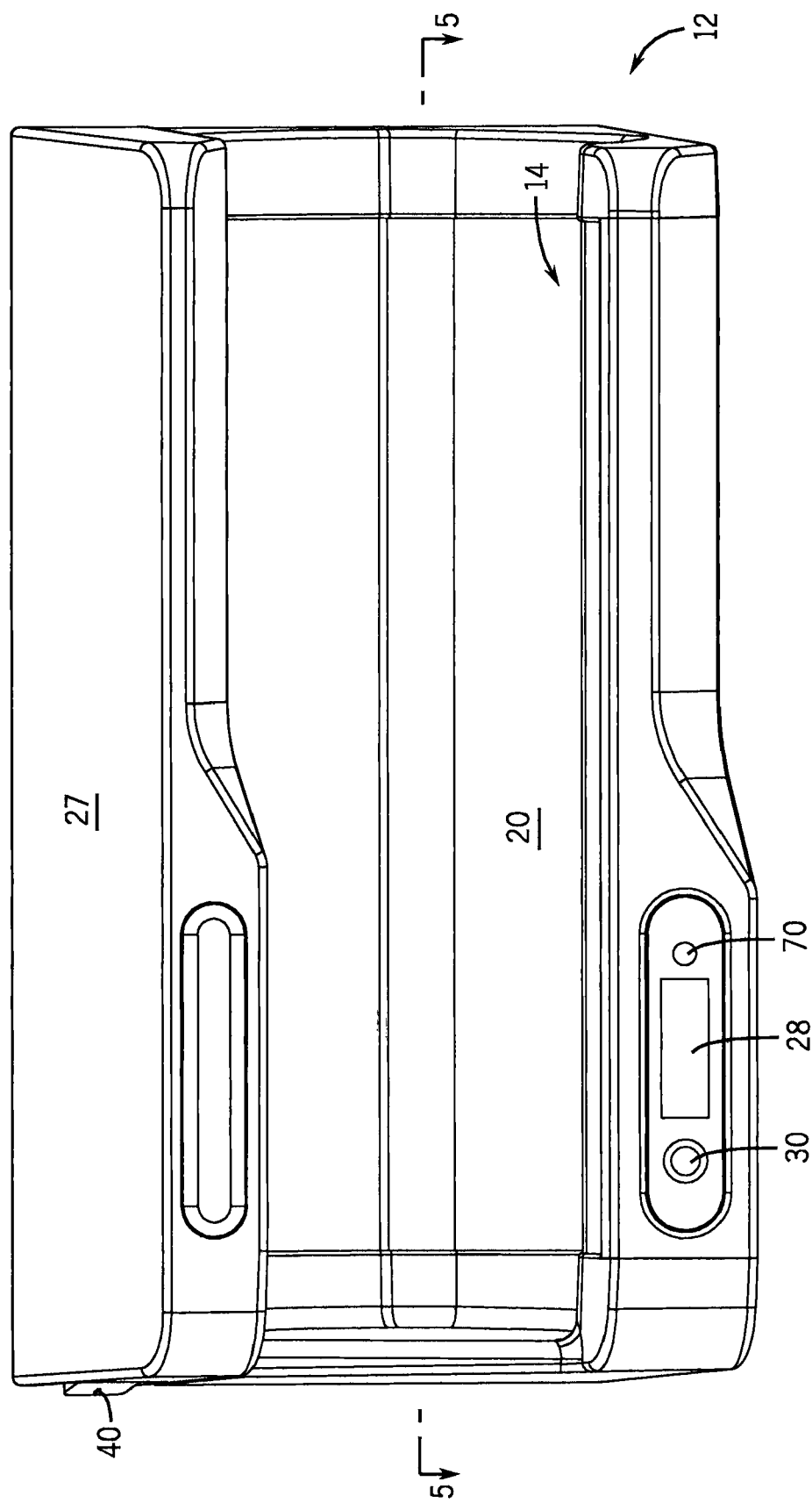
FIG. 4 is a front plan view of a modular fluid warmer.
Figure 5:
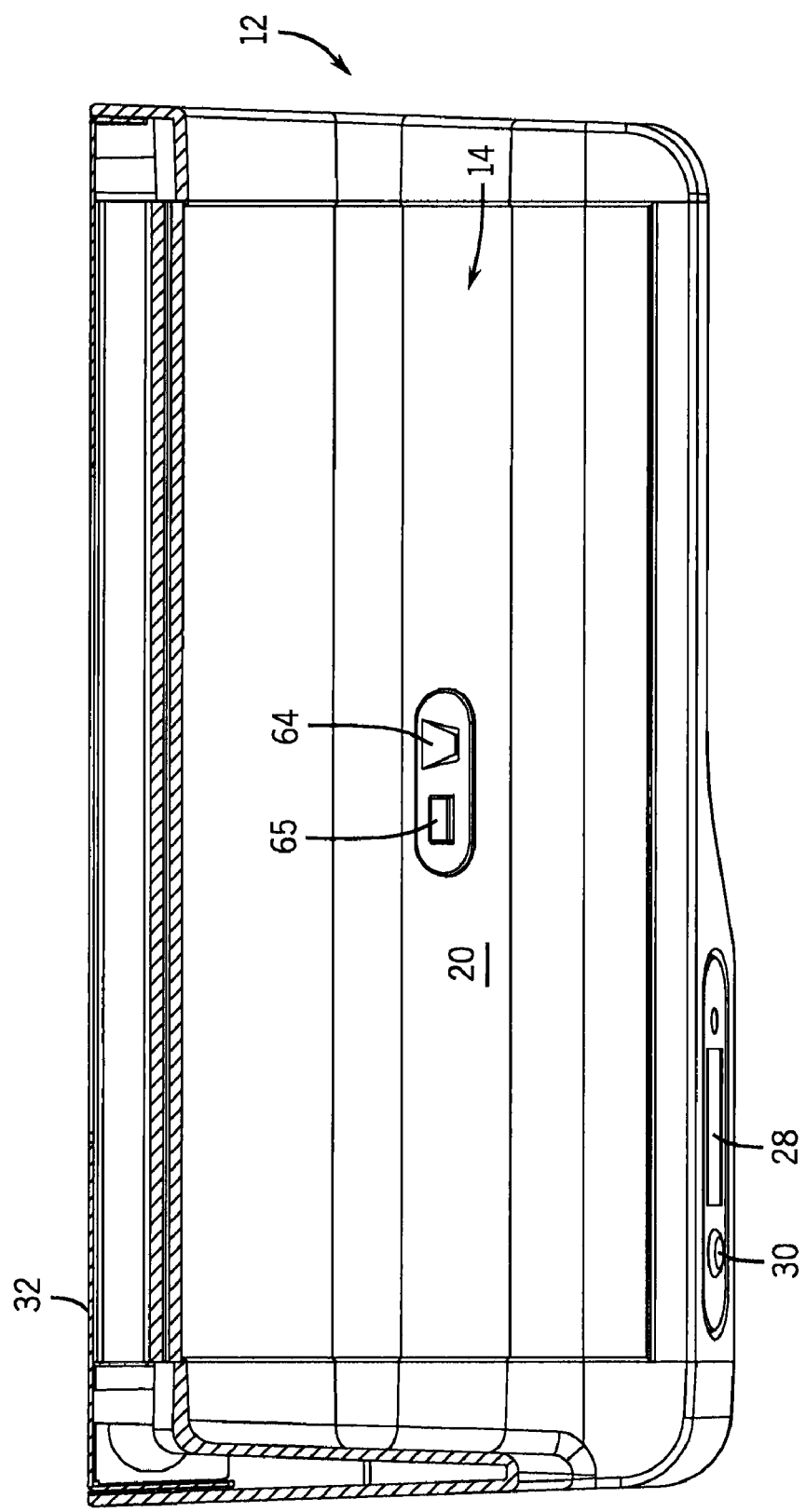
FIG. 5 is a cross sectional view of the modular fluid warmer along a line 5-5 showing an optical sensor and an item temperature sensor on the support surface.
Figure 6:
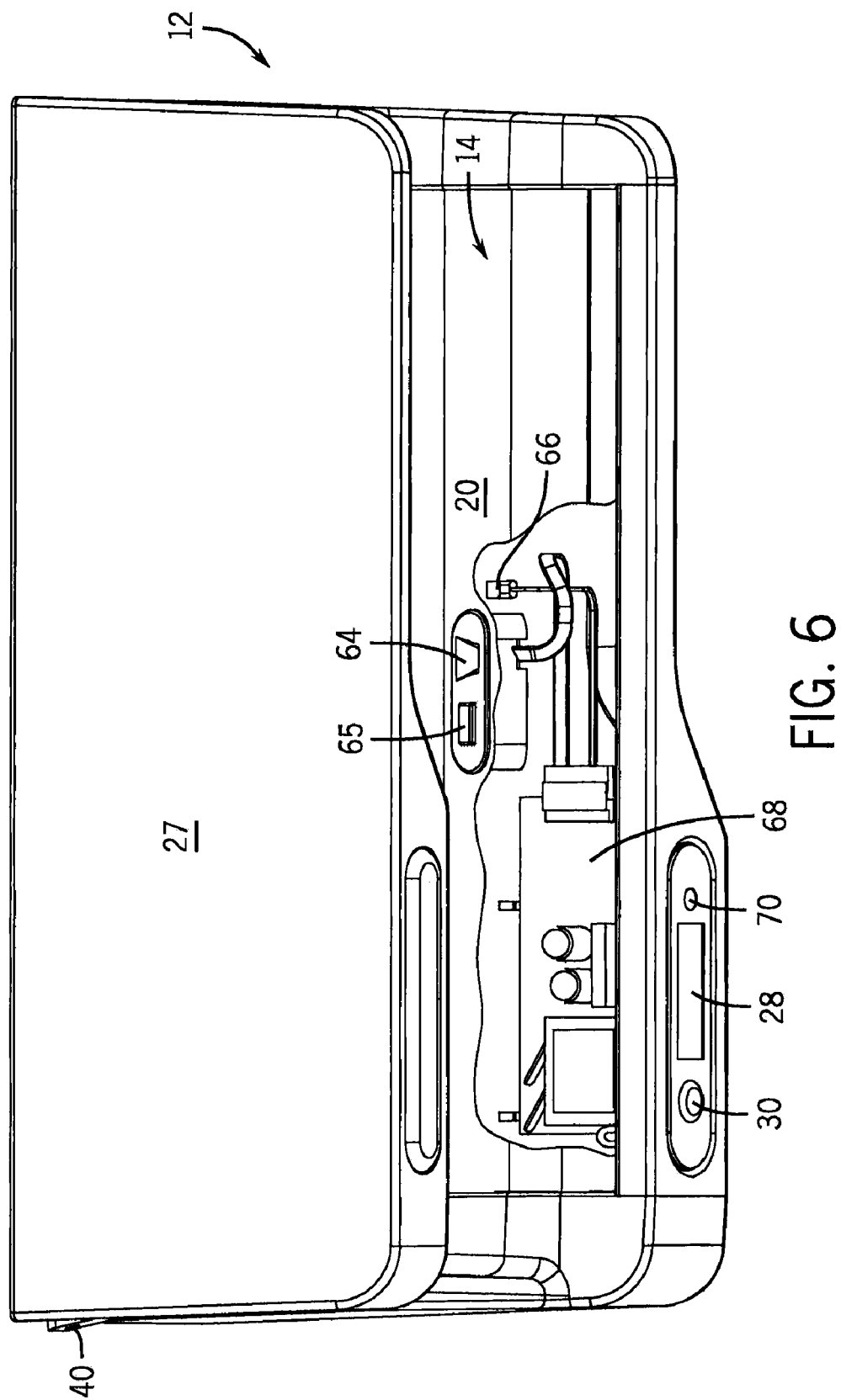
FIG. 6 is a cutaway view of the support surface of the modular fluid warmer to reveal the controller and wiring for various sensors.

Referring now to FIGS. 4-6, the sensors found on the support surface 20 can be seen. In particular, an optical item sensor 64 for detecting the presence of a container or item and an item temperature sensor 65 for measuring the temperature of the item received on the support surface 20 can be seen. As best seen in FIG. 6, there is also a heating element temperature sensor 66 for measuring the temperature of the heating element 23. All of these sensors are wired to the controller 68 which is located proximate the display 28.

In operation, when a container is received on the support surface 20, the optical item sensor 64 detects the container. When the optical item sensor 64 detects the container, the controller 68 starts the heating element 23 to heat the support surface 20. As the heating element 23 warms the support surface 20, the controller 68 continually reads the temperature of the container being heated using the item temperature sensor 65 and the heating element 23 using the heating element temperature sensor 66. Once the temperature of the container is within an appropriate temperature range for administration, then a timer in the controller 68 may start recording time to determine the length of time at which the container is maintained at the set point temperature of the modular fluid warmer 12. When the temperature of the container (and fluid therein) is within acceptable range for use, an LED light 70 on the front of the modular fluid warmer 12 may illuminate to indicate that the fluid is ready for administration. This indication could also be provided using the display 28.

Measuring time at temperature is generally preferable over measuring residence time, as the rate of degradation of the fluid is more closely related to the length of time at peak thermal temperatures than the total length of time in the modular fluid warmer 12. However, it is contemplated that the timer in the controller 68 could be configured to measure other time quantities, such as residence time or the like.

When the warmed container is removed from the support surface 20, the optical item sensor 64 detects that there is no longer an item on the support surface 20. This information is sent to the controller 69, which turns off the heating element 23 and resets any running timer. The modular fluid warmer 12 sits idle until another container is detected which restarts the heating element 23 and any other associated timing cycle.

As each of the modular fluid warmers 12 operate independently of one another, only the units in the stacked assembly 10 that are occupied by an item or container are heated. This provides flexibility in capacity and only requires the energy necessary to heat the occupied modular fluid warmers. Thus, the present invention provides efficient and selective warming of containers with little user interaction other than adding and removing the container from the support surface 20.

Figure 7:
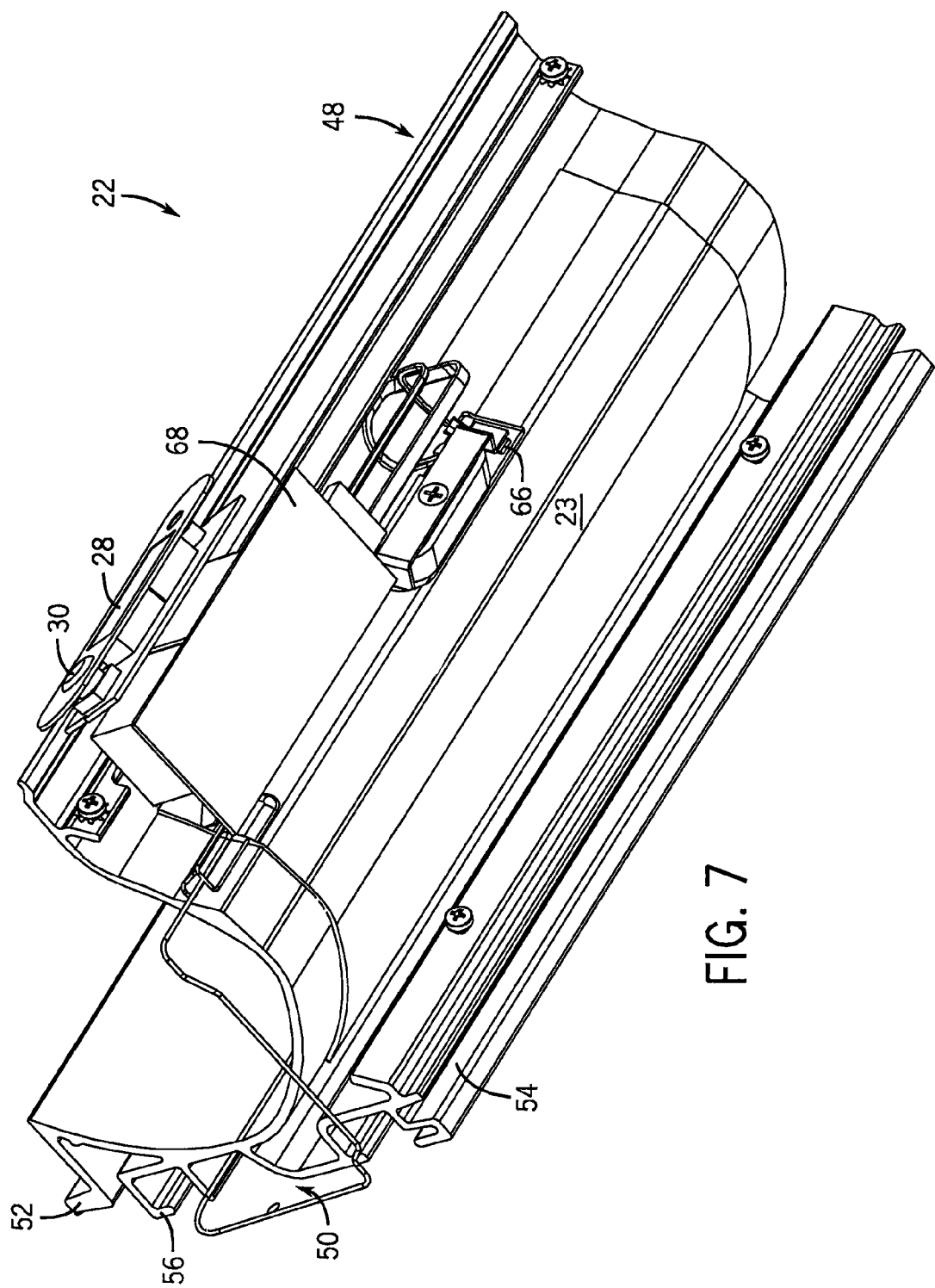
FIG. 7 is a front bottom perspective view of the modular fluid warmer with the plastic case removed to show the heating element on the underside of the support surface.
Figure 8:
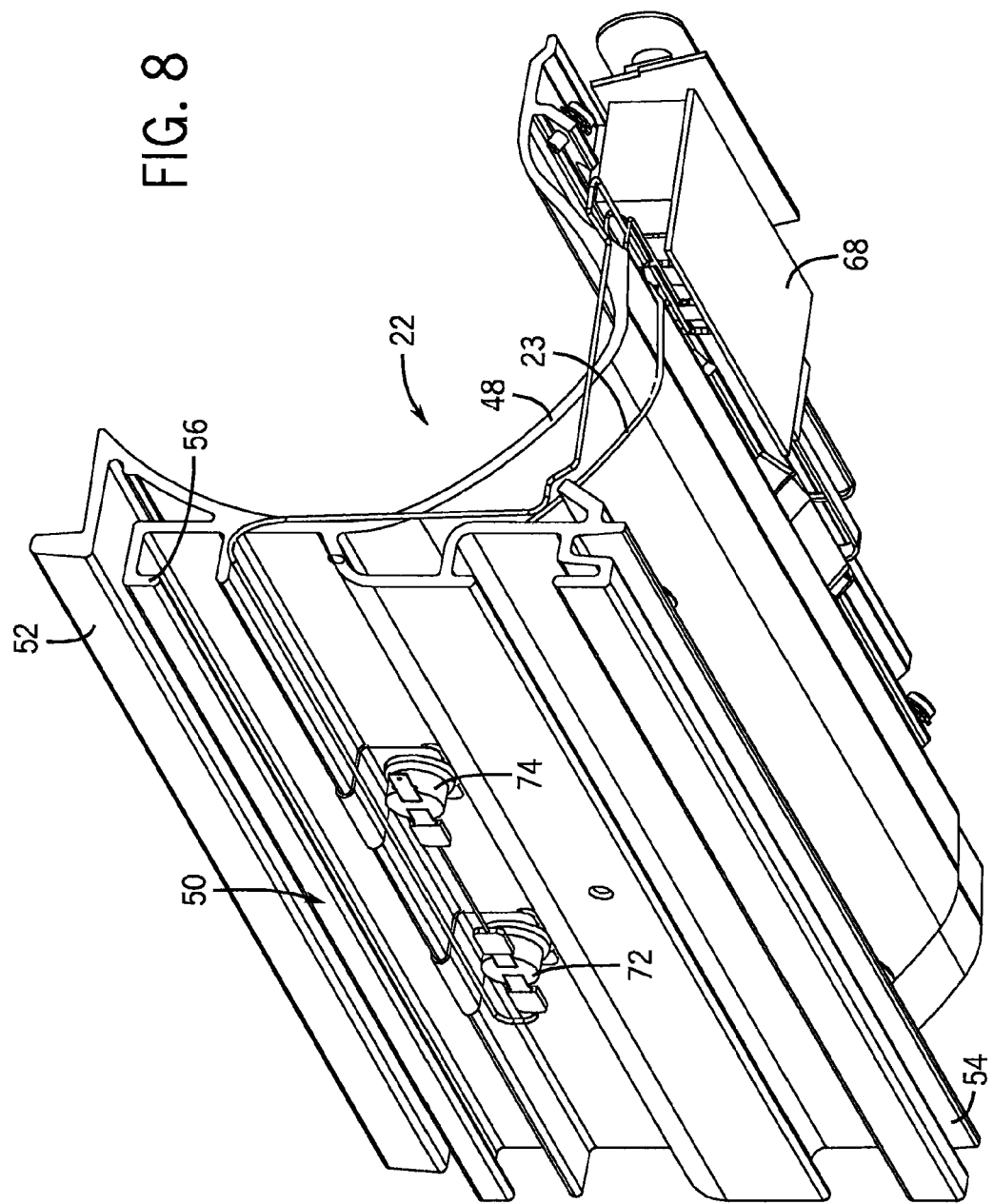
FIG. 8 is a rear bottom perspective view of the modular fluid warmer as in FIG. 7 showing the over temperature sensors on the back wall of the support structure.

Referring now to FIGS. 7 and 8, the support structure 22 is shown in more detail. As previously described, the support structure 22 includes the essentially C-shaped portion 48 and the back wall portion 50.

The support structure 22 may be comprised of aluminum and may be formed using an extrusion process. Although the support structure 22 may be formed of other materials, by other processes, or by joining separately formed components, using an aluminum extrusion process allows for an integrally formed support structure that can have complex features in cross section, such as the mating structures 52 and 54 and the tab 56.

FIGS. 7 and 8 most clearly show the heating element 23 wrapping around the underside of the essentially C-shaped portion 48 proximate the support surface 20. This heating element 23 may be a resistive heating element such as a silicon pad. However, other resistive materials or other types of heating elements could also be employed.

Referring specifically to FIG. 8, two support surface temperature sensors 72 and 74 are mounted on the back wall portion 50 of the support structure 22 proximate the support surface 20. These support surface temperature sensors 72 and 74 measure a temperature of the support structure 22 to ensure that the heating element 23 has not overheated. There is redundancy built into the number of sensors, such that if one of the sensors fails, there is at least one backup temperature sensor that will detect a faulty condition.

Figure 9:
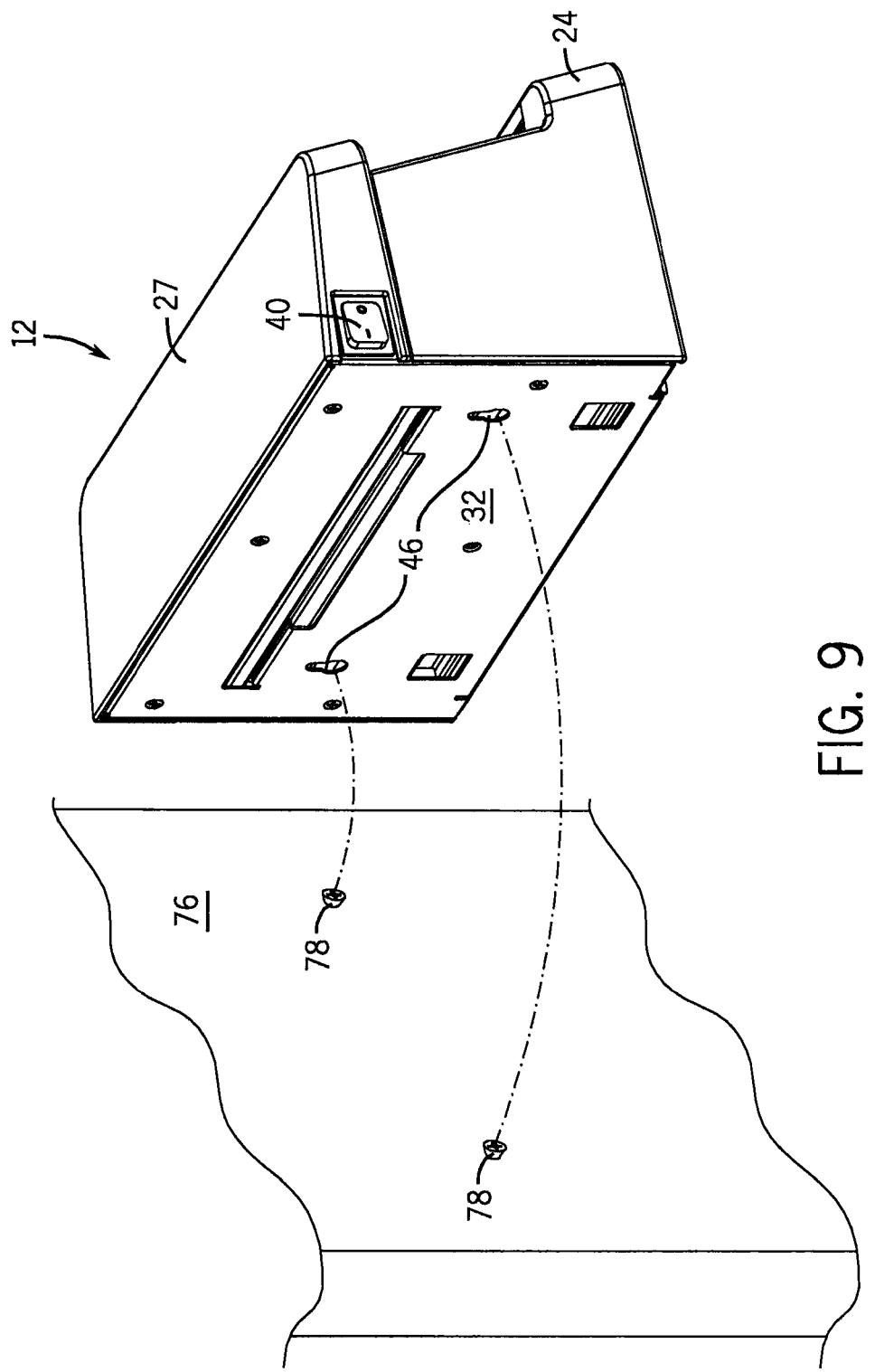
FIG. 9 is an environmental view of the modular fluid warmer being attached to a wall.
Figure 10:
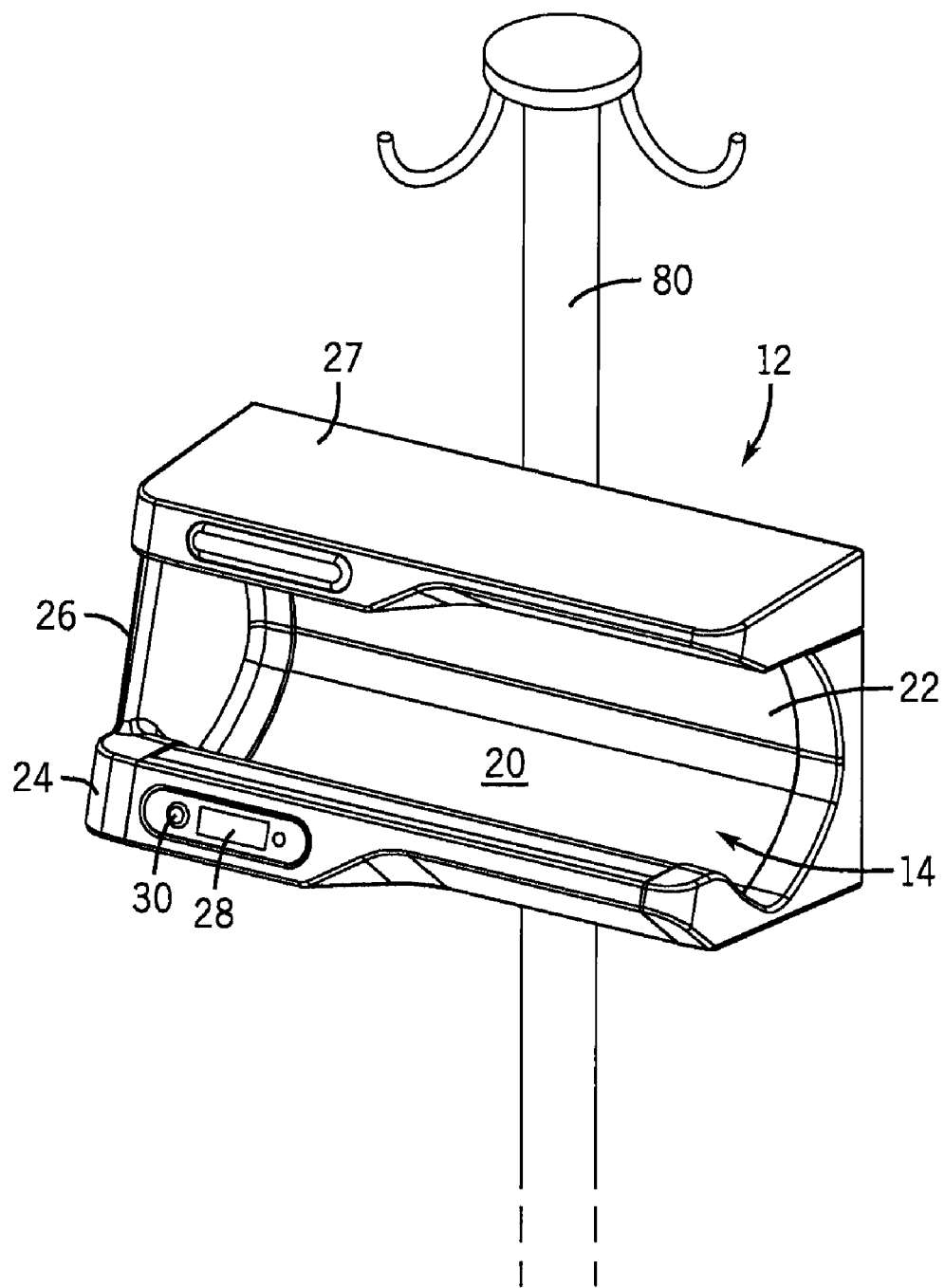
FIG. 10 is an environmental view of the modular fluid warmer attached to a moveable I.V. pole.

FIGS. 9 and 10 show some of the different ways in which the stacked assembly 10 can be supported other than sitting on a surface.

Referring now to FIG. 9, a modular fluid warmer 12 is shown mounted to a wall 76. The wall 76 has two screws 78 screwed part way into the wall 76. The mounting holes 46 in the back plate 32 of the modular fluid warmer 12 are pushed over the screws 78 and the modular fluid warmer 12 can be dropped into place to hang the modular fluid warmer 12 from the wall 76.

Referring now to FIG. 10, a modular fluid warmer 12 is shown attached to an I.V. pole 80. This I.V. pole 80 may include a number of caster wheels (not shown) at the base of the I.V. pole 80 so that the I.V. pole 80 can be transported. Attachment of the modular fluid warmer 12 to the I.V. pole 80 could be established in any one of a number of ways well known to those skilled in the art including hanging the modular fluid warmer 12 from a projection off of the I.V. pole 80, clamping the modular fluid warmer 12 using a collar to the I.V. pole 80, or the like.

It should be appreciated that while only a single fluid warmer has been shown as being mounted or attached to a wall or IV pole in FIGS. 9 and 10, that a stacked assembly 10 could likewise be attached in the same way. However, as the stacked assembly 10 has a back plate that is sized to match the number of shelves 14 in the stacked assembly 10, there may be more than one set of screws or the like to attach the stacked assembly 10 to the wall 76 or the I.V. pole 80.

Now with reference to FIGS. 11-16, a modified version of the modular fluid warmer 12 is shown having a switch assembly 82 for detection of an item on the support surface 20. In the embodiment of the modular fluid warmer 12 shown in FIGS. 11-16 the function of the optical item sensor 64 and the item temperature sensor 65 are integrated into a single switch assembly 82 to provide features not recited in the embodiments shown in FIGS. 1-10.

Figure 12:
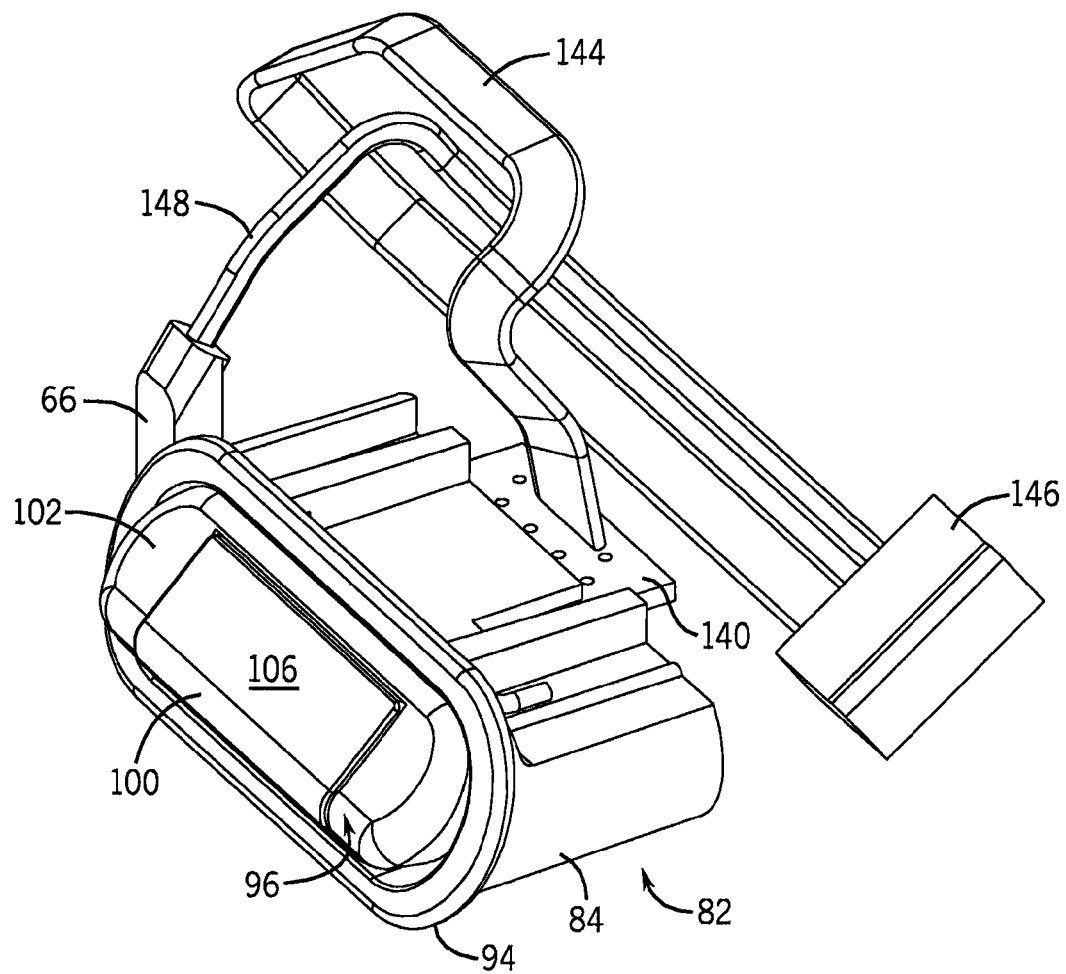
FIG. 12 is an isometric view of the switch assembly apart from the modular fluid warmer of FIG. 11.
Figure 13:
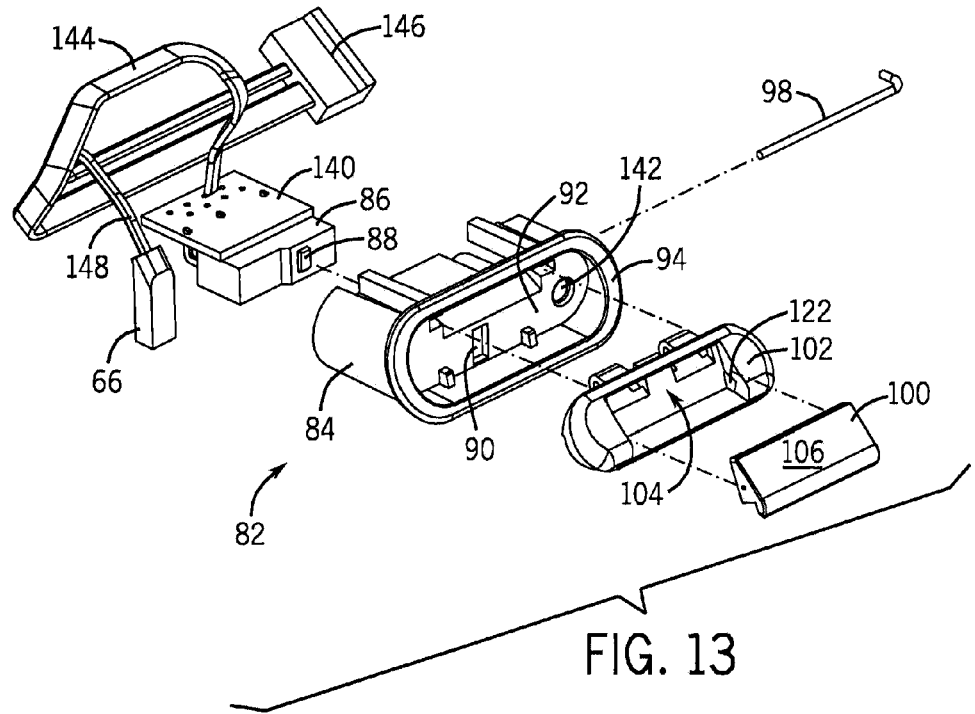
FIG. 13 is an exploded view of the switch assembly of FIG. 121
Figure 14:
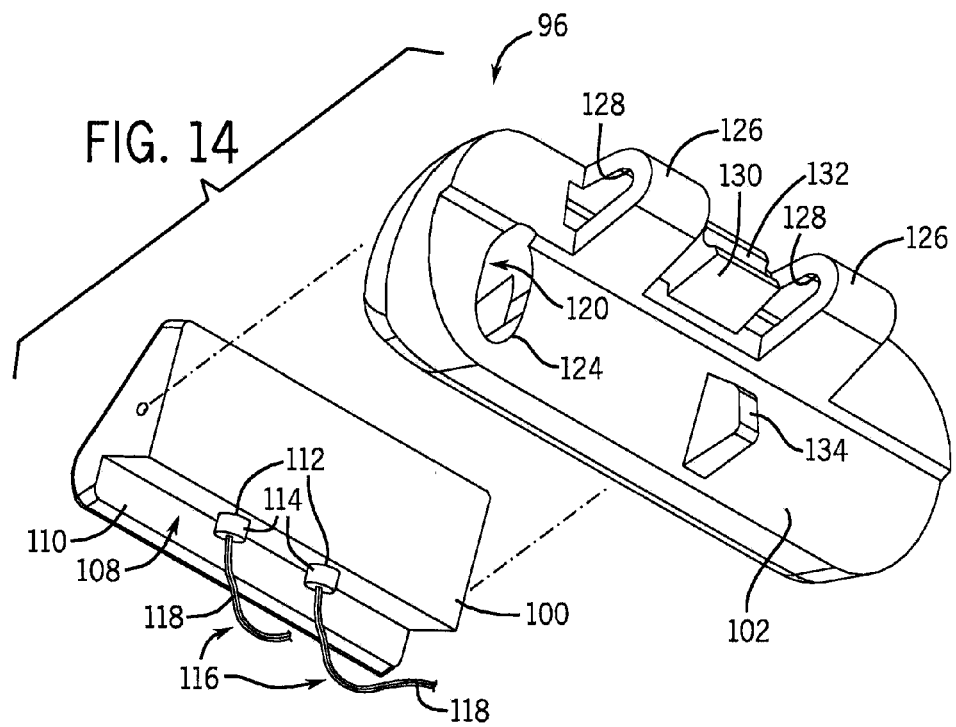
FIG. 14 is an exploded view of the movable switch plate of the switch assembly.
Figure 15:
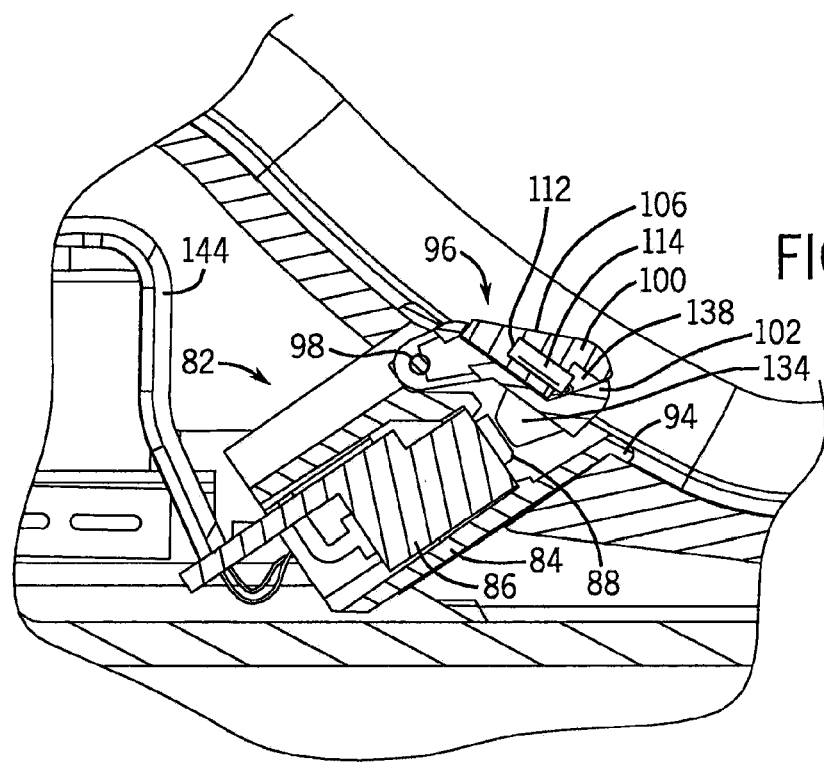
FIG. 15 is a cross sectional side view taken through line 15-15 of FIG. 11 in which the switch is not depressed.
Figure 16:
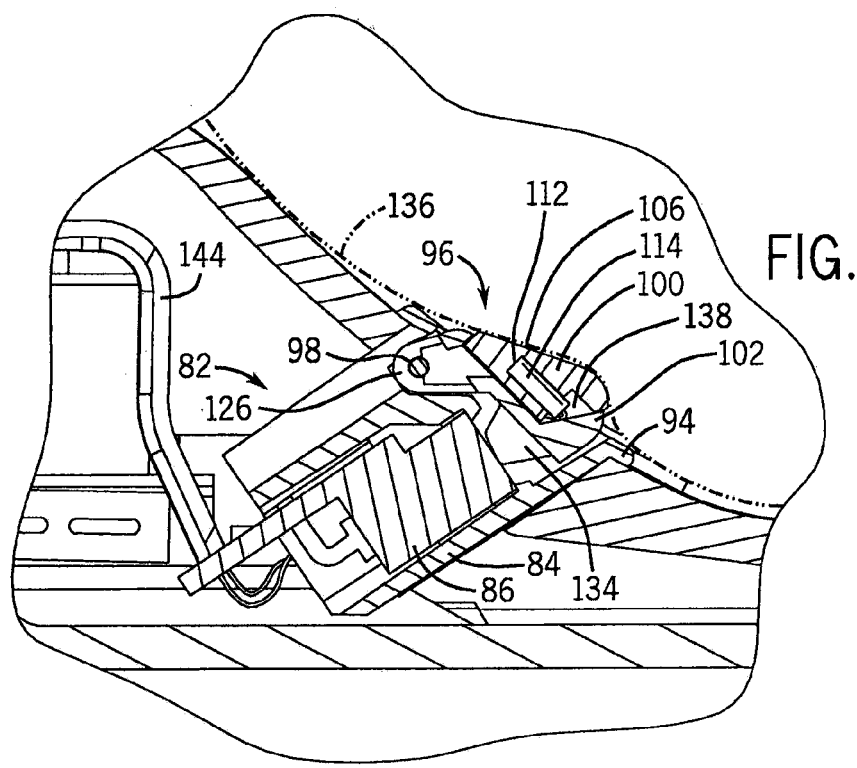
FIG. 16 is a cross sectional side view similar to FIG. 15, but in which a bag of intravenous fluid or the like has been placed on the support surface thereby depressing the switch.

Specifically referring to FIGS. 12-16, the details of the switch assembly 82 are shown. The switch assembly 82 includes a switch housing 84 that receives a switch 86. In the form shown, the switch 86 is a microswitch having an actuatable portion in the form of a button 88 which may be mechanically displaced to alter or change the state of the switch 86. Of course, other types of switches may also be used in the place of this microswitch. As best shown in FIGS. 13, 15, and 16, the switch 86 is inserted into the switch housing 84 from a bottom side of the switch housing 84. The button 88, which is actuatable in a direction parallel to the direction of insertion of the switch 86 into the switch housing 84, is positioned in a slot 90 that is formed in an internal wall 92 of the switch housing 84. Preferably, the internal wall 92 prevents the body of the switch 86 from passing through the switch housing 84 during insertion. The switch housing 84 also includes a flange 94 which positions the top end of the switch assembly 82 relative to support surface 20 of fluid warmer 12 in which the switch assembly 82 is received. This flange 94 ensures that a portion of the switch assembly 82 extends above the support surface 20 so that an item placed on this switch assembly 82 will contact this portion.

Figure 11:
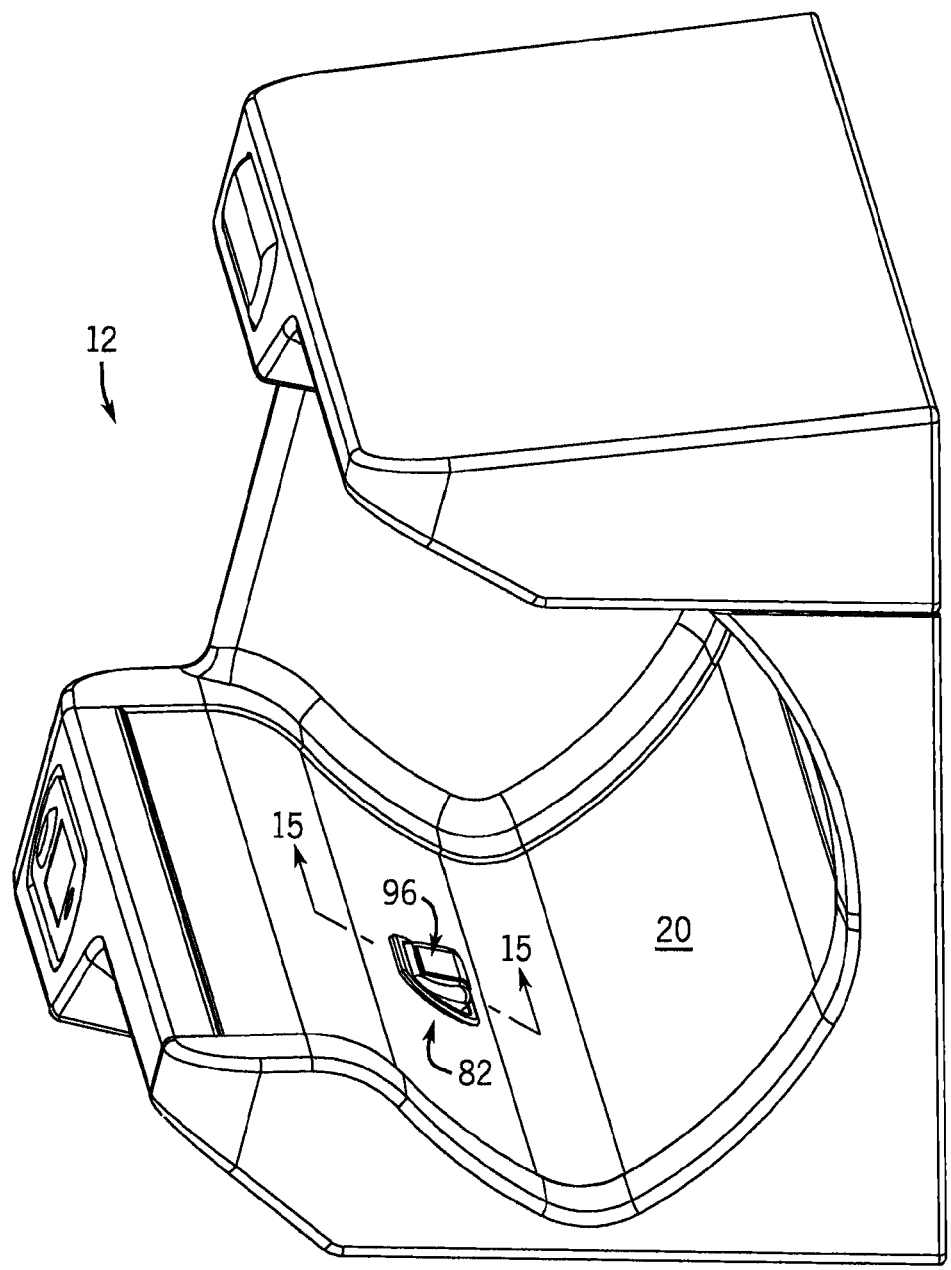
FIG. 11 is a perspective view of an alternative embodiment of the modular fluid warmer with a switch assembly having an embedded thermocouple.

On the top end of the switch assembly 82, there is a movable switch plate 96 which, as illustrated in FIG. 11, extends upwardly from the support surface 20 of the fluid warmer 12. A pivot pin 96 pivotally connects the movable switch plate 96 to the switch housing 84 on the side of the switch housing 84 opposite the side of the switch housing 84 that the switch 86 is inserted into. The movable switch plate 96 is two-part in construction and includes a heat conducting member 100 and a receptor member 102 that has a cavity 104. The heat conducting member 100 is shaped and sized to be received in the cavity 104 of the receptor member 102. The heat conducting member 100 may be retained in the receptor member 102 in any of a number of ways including, for example, designing the two components to have an interference fit with one another, adhering the two components together, using one or more fasteners to join the components to one another, and so forth.

The heat conducting member 100 is preferably formed of a material having a high thermal conductivity such as, for example, copper or a copper alloy. The heat conducting member 100 could also be made of other materials having a high thermal conductivity including, for example, materials having a thermal conductivity value, k, exceeding $200 \text{ W·m}^{-1}\text{·K}^{-1}$ or materials having a thermal conductivity value exceeding approximately $200 \text{ W·m}^{-1}\text{·K}^{-1}$.

The heat conducting member 100 includes a body having an upper contact surface 106 for contacting an item placed on the support surface 20 of the fluid warmer 12. On a generally opposing face of the heat conducting member 100, a recess 108 is formed on one end of the bottom face of the body thereby forming an overhanging section 110. Two bays 112 are formed in one of the walls of the recess 108. The two bays 112 are cylindrically-shaped holes which extend into, but not through, the heat conducting member 100 toward the contact surface 106. The probe ends 114 of two separate thermocouples 116 are received into the two bays 112. As illustrated in FIG. 14, a pair of wires 118 extend from each thermocouple 116.

It should be appreciated that the probe ends 114 of the thermocouples 116 each include a hot juncture between two different kinds of wire material that provide a readable voltage differential. This voltage differential is dependent on the temperature at the hot juncture. As shown in FIGS. 15 and 16, the probe ends 114 are inserted into the bays 112 of heat conducting member 100 to locate the hot juncture of the thermocouples 116 both within the heat conducting member 100 and below the contact surface 106 of the heat conducting member 100. Although not illustrated, the hot juncture may be located either within the probe ends 114 or outside the probe ends 114 but inside the bays 112.

In any event, the hot juncture of the thermocouple 116 should be in thermal communication with any item placed on the contact surface 106 via the heat conducting member 100 so as to readily allow heat transfer from an item on the contact surface 106 to the hot juncture of the thermocouple 116. In this way, the thermocouple 116 may accurately read the temperature of the item placed on the contact surface 106 within a predetermined period of time.

This predetermined amount of time will be based on a number of variables related to heat transfer and the particular dimensions of the structure. For example, all other conditions being equal, the higher the thermal conductivity of the heat conducting member 100, the more quickly an accurate temperature reading will be obtained by the thermocouples 116 within each of the bays 112. Likewise, the closer the hot junctures of each of the thermocouples 116 are to the contact surface 106 of the heat conducting member 100, the more quickly the thermocouples 116 with detect an accurate temperature of the item placed on the contact surface 106, as the length of the path of conductance is shortened. Of course, one having skill in the art will appreciate that the temperature read by the thermocouple 116 will not be completely accurate due to, among other things, heat loss over the path of conductance or transmission. However, with the structure described herein, a sufficiently accurate and precise reading of the temperature should be obtainable with a predetermined length of time for the practical purpose of monitoring the temperature of the item on the support surface 20.

Turning now to the receptor member 102 of the movable switch plate 96, the receptor member 102 may be made of any of a number of materials including, for example, an injection molded plastic material. The material should be selected, however, to be structurally stable under prolonged exposure to the temperatures of the support surface 20 and the item being supported on the switch assembly 82. The receptor member 102 includes a passage 120 running from an entrance opening 122 in the cavity 104, through the body of the receptor member 102, and to an exit opening 124 on the underside (best seen in FIG. 14) of the receptor member 102. As also seen in FIG. 14, on one side of the underside of the receptor member 102, two loops 126 with inner bearing surfaces 128 and an outwardly extending post 130 with a concave bearing surface 132 are configured to receive the pivot pin 98. As mentioned above, the pivot pin 98 defines the rotational axis for the movable switch plate 96 relative to the switch housing 84.

The underside of the receptor member 102 also has a projection 134 formed therein which is positioned to contact the button 88 of the switch 86. As illustrated in FIG. 15, when nothing is placed on either the support surface 20 or the contact surface 106 of the movable switch plate 96, then the button 88 of the switch 86 is biased into a first state, an up position, hereby indicating an item is not present on the contact surface 106. However, as shown in FIG. 16, when an item, such as a bag of fluid, as indicated by the phantom line 136, is place on top of the support surface 20 for heating, the weight of this item on the contact surface 106 of the movable switch plate 96 causes the movable switch plate 96 to pivot downwardly about the pivot pin 98. This downward pivoting results in the projection 134 of the movable switch plate 96 depressing the button 88 of the switch 86 into a second state, a down position, indicating the presence of an item on the contact surface 106.

Notably, both the heat conducting member 100 and the receptor member 102 are also constructed to accommodate the passage of the wires 118 of the thermocouples 116 there through. When the heat conducting member 100 is inserted into the cavity 104 of the receptor member 102, an open space 138 is formed between the recess 108 of the heat conducting member 100 and the cavity 104 of the receptor member 102. This open space 138 is best seen in the cross section of FIGS. 15 and 16 and provides a pathway for the wires 118 of the thermocouples 116 to extend from the bays 112 in the heat conducting member 100, through the open space 138 to the entrance opening 122 of the passage 120 in the receptor member 102, through the passage 120, and out of the exit opening 124 of the receptor member 102. In this way, the wires 118 from the thermocouples 116 can be routed through and out of the movable switch plate 96 from the underside of the movable switch plate 96, thereby concealing the wires 118 of the thermocouples 116 from plain view.

The wires 118 then extend through the switch housing 84 and connect to a printed circuit board 140 which is mounted to the switch 86. The internal wall 92 of the switch housing 84 includes a hole 142 through which the wires 118 are routed so that they run through the switch housing 84 on one of the lateral sides of the switch 86. The hole 142 is positioned such that, when the switch assembly 82 is assembled, the hole 142 generally aligns with the exit opening 124 of the movable switch plate 96. With this alignment, the wires 118 running out of the exit opening 124 are then easily directed through the hole 142 in the switch housing 84. After passing through the hole 142 and out of the bottom of the switch housing 84, the wires 118 are electrically connected, such as by solder, to the printed circuit board 140.

The switch 96 is also in electrical communication with the printed circuit board 140. In particular, the state of the switch 96 may be sent as a signal to the printed circuit board 140.

As best seen in FIG. 12, a multiconductor cable 144 is attached to the printed circuit board 140 which extends to a plug 146 for connection to the controller 68. The multiconductor cable 144 carries signals related to state of the switch 86 (i.e., is the movable switch plate 96 depressed indicating the presence of an item on the support surface 20) as well as the temperature of the two thermocouples 116 embedded under the contact surface 106 of heat conducting member 100.

In the form shown, an additional cable 148 also extends from the plug 146. This cable 148 is attached to the heating element temperature sensor 66. Although in the embodiment shown, a single plug is shown that is attached to multiple cables, those having ordinary skill in the art will appreciate that each sensor could have a separate connector or plug or that further sensors and their related cables could be joined at a single plug.

There are many advantages to the switch assembly 82 described above. This switch assembly 82 may be used to detect the presence of an item, such as a bag of fluid, on the support surface 20 and automatically turn the fluid warmer 12 on or off (i.e., turn on or off the heating element 23) based on a presence state. Among other thing, this helps to conserve energy as the fluid warmer 12 only heats the support surface 20 when an item is placed on it.

Further, this switch assembly 82 senses the temperature of the contents of the item by direct contact of the item with the heat conducting member 100, giving an accurate temperature reading. Notably, an air gap exists between the movable switch plate 96 and the support surface 20 of the fluid warmer 12, that thermally isolates the thermocouples 116 from heating elements 23 and thereby results in a more accurate temperature reading.

The switch assembly 82 also includes two thermocouples 116 so that the controller 86 may compare the signals provided by both thermocouples 116 to one another. In the event that one thermocouple signal deviates significantly from another (by a value that may be predetermined), the fluid warmer 12 may shut down and/or provide a message to indicate that the unit needs servicing. This prevents operating the unit in situation where a single thermocouple has been corrupted. Especially for biological fluids, spoilage may be an significant issue if the device operates outside of its prescribed temperature range. Of course, it is also contemplated that only a single thermocouple might be used in the switch, although the above-stated advantage would be lost.

Accordingly, the switch assembly 82 disclosed above is able to both detect the presence of an item on the contact surface 106 of the switch assembly 82 as well as detect the temperature of the item on the contact surface 106 via the thermocouples 116 embedded below the contact surface 106. Both the switch 86 and the thermocouples 116 may be in electrical communication with the printed circuit board 140 which collects and sends the presence and temperature signals from them to the controller 68. The data collected by the controller 68 may be used in a number of ways including to track the thermal history of the item on the fluid warmer 12, to initiate and regulate the heating of the item on the fluid warmer 12, and so forth.

While the switch assembly 82 has been disclosed as for a fluid warmer 12, one having skill in the art will appreciate that the switch assembly 82 may also be incorporated in any number of other applications in which presence and temperature detection are required. These applications need not be limited to warming application, but could also include cooling applications.

It should be appreciated that various other modifications and variations to the preferred embodiments can be made within the spirit and scope of the invention. Therefore, the invention should not be limited to the described embodiments. To ascertain the full scope of the invention, the following claims should be referenced.

What is claimed is:

1. A fluid warmer comprising:
a support surface;
a heating element configured to selectively heat the support surface; and
a switch assembly extending through the support surface, the switch assembly including a switch having at least two states, one of the at least two states indicating a presence of an item on the support surface and further including a movable switch plate operably linked to the switch to move the switch between the at least two states, the movable switch plate including a contact surface that contacts an item placed on the support surface; and
a temperature sensor attached to and in thermal communication with the movable switch plate;
wherein the movable switch plate comprises a material having a thermal conductivity that permits the temperature sensor embedded in the switch plate to measure a temperature of an item placed on the support surface within a predetermined period of time.

2. The fluid warmer of claim 1, wherein the movable switch plate comprises a heat conducting member in which an end of the temperature sensor is embedded and wherein the heat conducting member also forms at least a portion of the contact surface of the movable switch plate.

3. The fluid warmer of claim 2, wherein the heat conducting member comprises a material having a thermal conductivity exceeding 200 $Wm^{-1}K^{-1}$.

4. The fluid warmer of claim 2, wherein the heat conducting member comprises copper.

5. The fluid warmer of claim 1, wherein the movable switch plate includes a first portion and a second portion and wherein a cavity formed in the second portion that receives the first portion.

6. The fluid warmer of claim 5, wherein the first portion has at least one bay formed therein that receives an end of the temperature sensor.

7. The fluid warmer of claim 6, wherein, when the first portion is received in the second portion, a space is defined between the first portion and the second portion.

8. The fluid warmer of claim 7, wherein the second portion includes a passage running from the cavity through the second portion, thereby providing a pathway for a wire of the temperature sensor from the at least one bay in the first portion, through the space between the first portion and the second portion, and through the passage in the second portion to an exterior of the movable switch plate.

9. The fluid warmer of claim 1, wherein a thermal insulator separates the movable switch plate from the support surface of the fluid warmer, thereby thermally isolating the movable switch plate from the support surface of the fluid warmer.

10. The fluid warmer of claim 1, wherein the movable switch plate includes a downwardly extending projection that engages an actuatable part of the switch.

11. The fluid warmer of claim 1, wherein the switch assembly further includes a switch housing that supports the switch and the movable switch plate.

12. The fluid warmer of claim 11, wherein the movable switch plate is pivotally attached to the switch housing.

13. The fluid warmer of claim 12, wherein the movable switch plate is pivotally attached to the switch housing by a pivot pin.

14. The fluid warmer of claim 11, wherein the switch housing includes a flange which is configured to position the switch assembly relative to a support surface of the fluid warmer such that the contact surface of the movable switch plate resides above the support surface.

15. The fluid warmer of claim 1, wherein the switch and movable switch plate constitute a presence sensor configured to detect the item on the contact surface.

16. The fluid warmer of claim 15, wherein the presence sensor provides a signal indicating the item is disposed on the contact surface and the temperature sensor provides a signal indicating a temperature of the item disposed on the contact surface.

17. The fluid warmer of claim 1 wherein the support surface is open to the air without an obstructing cover.

18. The fluid warmer of claim 17 wherein the support surface is held within a housing providing a portion extending over the support surface and providing a horizontally accessible opening to the support surface.

19. The fluid warmer of claim 1 further including at least a second temperature sensor co-located in the movable switch plate and further including a circuit comparing signals from the at least two temperature sensors to detect a deviation thereamong.

\* \* \* \* \*